United States Patent
Sai et al.

(10) Patent No.: US 11,059,799 B2
(45) Date of Patent: Jul. 13, 2021

(54) PROCESS FOR PREPARATION OF ERIBULIN AND INTERMEDIATES THEREOF

(71) Applicant: DR. REDDY'S LABORATORIES LIMITED, Hyderabad (IN)

(72) Inventors: Sudhir Sai, Hyderabad (IN); Debjit Basu, Hyderabad (IN); Kumar Sarvesh, Secunderabad (IN); Uday Kumar Neelam, Hyderabad (IN); Amit Kumar Mandal, Hyderabad (IN); Rakeshwar Bandichhor, Sultanpur (IN); Vilas Hareshwar Dahanukar, Hyderabad (IN)

(73) Assignee: DR. REDDY'S LABORATORIES LIMITED., Hyderabad (IN)

( * ) Notice: Subject to any disclaimer, the term of this patent is extended or adjusted under 35 U.S.C. 154(b) by 0 days.

(21) Appl. No.: 16/304,470

(22) PCT Filed: May 25, 2017

(86) PCT No.: PCT/IB2017/053082
§ 371 (c)(1),
(2) Date: Nov. 26, 2018

(87) PCT Pub. No.: WO2017/203459
PCT Pub. Date: Nov. 30, 2017

(65) Prior Publication Data
US 2019/0177291 A1 Jun. 13, 2019

(30) Foreign Application Priority Data

May 26, 2016 (IN) .............................. 201641018136
Jun. 22, 2016 (IN) .............................. 201641021480

(51) Int. Cl.
C07D 307/28 (2006.01)
C07D 493/22 (2006.01)
C07F 7/18 (2006.01)
C07C 233/18 (2006.01)

(52) U.S. Cl.
CPC .......... *C07D 307/28* (2013.01); *C07C 233/18* (2013.01); *C07D 493/22* (2013.01); *C07F 7/1804* (2013.01)

(58) Field of Classification Search
CPC .................................................. C07D 307/28
See application file for complete search history.

(56) References Cited

U.S. PATENT DOCUMENTS 6,214,865 B1 4/2001 Littlefield et al.
6,469,182 B1 10/2002 Littlefield et al.
8,445,701 B2 5/2013 Austad et al.

FOREIGN PATENT DOCUMENTS

| CN | 105713031 A | 6/2016 | | |
|---|---|---|---|---|
| IN | 3529/CHE/2013 A | 2/2015 | | |
| WO | 2005/118565 A1 | 12/2005 | | |
| WO | WO-2005118565 A1 * | 12/2005 | .............. | A61P 35/02 |
| WO | 2013/142999 A1 | 10/2013 | | |
| WO | 2017/064627 A2 | 4/2017 | | |
| WO | WO-2017064627 A2 * | 4/2017 | .............. | A61K 31/00 |
| WO | 2017/203459 A1 | 11/2017 | | |
| WO | WO-2018096478 A2 * | 5/2018 | ........... | C07D 493/04 |

OTHER PUBLICATIONS

Martin, M.J., et al. "Stellatolides, a New Cyclodepsipeptide Family from the Sponge *Ecionemia acervus*: Isolation, Solid-Phase Total Synthesis, and Full Structural Assignment of Stellatolide A." J. Am. Chem. Soc. (2014), vol. 136, pp. 6754-6762. (Year: 2014).*
Jackson, K.L., et al. "A Total Synthesis of Norhalichondrin B." Angew Chem. Int. Ed. Engl. (2009), vol. 48, Issue 13, pp. 2346-2350. (Year: 2009).*
International Search Report dated Sep. 19, 2017, for corresponding International Patent Application No. PCT/IB2017/053082.
Written Opinion dated Sep. 19, 2017, for corresponding International Patent Application No. PCT/IB2017/053082.
International Preliminary Report on Patentability dated Nov. 27, 2018, for corresponding International Patent Application No. PCT/IB2017/053082.
International Search Report dated May 31, 2018, for International Patent Application No. PCT/IB2017/057352, U.S. Appl. No. 16/463,727.
Written Opinion dated May 31, 2018, for International Patent Application No. PCT/IB2017/057352, U.S. Appl. No. 16/463,727.
International Preliminary Report on Patentability dated May 28, 2019, for International Patent Application No. PCT/IB2017/057352, U.S. Appl. No. 16/463,727.
Herbert C. Brown et. al., "Asymmetric Reduction with Chiral Organoboranes Based on alpha-Pinene", Acc. Chem. Res., vol. 25, No. 1, 1992.
Aicher, Thomas, Synthesis of Halichondrin B Norhalichondrin B, Harvard University, Cambridge MA J. Am. Chem. Soc. 1992, 114, pp. 3162-3164.
Bonini, Carlo, New Functionalized Hydroxymethyl Ketones from the Mild and Chemoselective KMnO4 Oxidation of Chiral Terminal Olefins., Eur.J. Org. Chem., 2006 pp. 80-83.
Habrant, Damien, Conversion of Carbonyl Compounds to Alkynes: General Overview and Recent Developments, Chem. Soc. Rev., 2010, 39, 2007-2017, Mar. 24, 2010.
Jiang, et al., A Novel Route to the F-Ring of Halichondrin B Diastereoselection in Pd(0)-Mediated Meso and C2 Diol Desymmetrization, Organic Letters, 2002 vol. 4, No. 20, 3411-3414.
Yu, Melvin, et al., From Micrograms to Grams: Scale-Up Synthesis of Eribulin Mesylate, Nat. Prod. Rep., 2013, 30, 1158-1164, Jul. 30, 2013.

* cited by examiner

*Primary Examiner* — John S Kenyon
(74) *Attorney, Agent, or Firm* — Pergament & Cepeda LLP; Milagros A. Cepeda; Edward D. Pergament

(57) ABSTRACT

The present application relate to a process for preparation of 4-Methylene tetrahydrofuran compound of formula II, which is useful as an intermediate for the preparation of halichondrin B analogues such as Eribulin.

7 Claims, No Drawings

PROCESS FOR PREPARATION OF ERIBULIN AND INTERMEDIATES THEREOF

This application is a National Stage Application under 35 U.S.C. § 371 of PCT International Application No. PCT/162017/053082, filed May 25, 2017, which takes priority from Indian Provisional Application Numbers IN 201641018136, filed May 26, 2016; and IN 201641021480, filed Jun. 22, 2016, all of which are herein incorporated in their entireties.

Aspects of the present application relate to a process for preparation of 4-Methylene tetrahydrofuran compound of formula II, which is useful as an intermediate for the preparation of halichondrin B analogues such as Eribulin.

The drug compound having the adopted name Eribulin, is a synthetic analogue of halichondrin B, and is represented by structure of formula I.

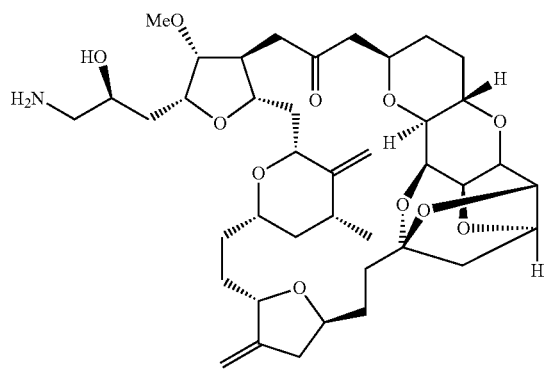

Eribulin is a microtubule inhibitor indicated for the treatment of patients with metastatic breast cancer who have previously received at least two chemotherapeutic regimens for the treatment of metastatic disease. U.S. Pat. No. 6,214,865 discloses eribulin and its pharmaceutically acceptable salts. 4-Methylene tetrahydrofuran compound of formula II used as an intermediate for the preparation of halichondrin B analogues such as Eribulin.

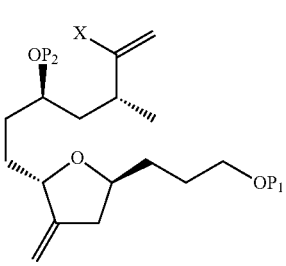

wherein $P_1$ is H or an alcohol protected group; $P_2$ is H or an alcohol protected group or $-SO_2(R_1)$; wherein $R_1$ is selected from straight or branched $C_1$-$C_{10}$ alkyl or optionally substituted $C_5$-$C_{12}$ aryl; X is halogen.

Process for the preparation of 4-Methylene tetrahydrofuran compound of formula II have been disclosed in PCT application No. 2005/118565A1, *J. Am. Chem. Soc.*, 1992, 114, 3162 and *Org. Lett.*, 2002, 4, 3411-3414. The reported processes suffer from major disadvantages, including use of highly expensive reagents, large amounts of catalysts, low temperature and longer reaction time.

Hence, there remains a need to provide an alternative processes for the preparation of 4-Methylene tetrahydrofuran compound of formula II, which is simple, economic and industrially viable, which in turn can be converted to Eribulin.

SUMMARY

In the first embodiment, the present application provides a process for preparation of 4-Methylene tetrahydrofuran compound of formula II,

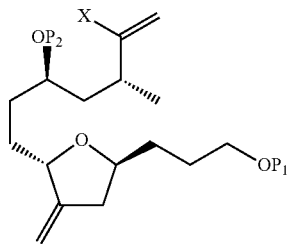

wherein $P_1$ is H or an alcohol protecting group; P2 is H or an alcohol protecting group or $-SO_2(R_1)$; wherein $R_1$ is selected from straight or branched $C_1$-$C_{10}$ alkyl or optionally substituted $C_5$-$C_{12}$ aryl; X is halogen;

which includes one or more of the following steps:
(a) reacting compound of formula III with compound of formula IV to provide compound of formula V;

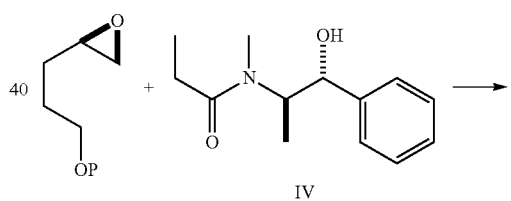

wherein P is an alcohol-protecting group;
(b) protecting compound of formula V to provide compound of formula VI;

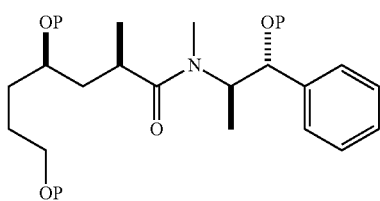

VI wherein P is an alcohol-protecting group;

(c) deprotecting compound of formula VI to provide compound of formula VII;

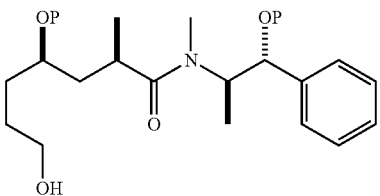

VII wherein P is an alcohol-protecting group;

(d) converting compound of formula VII to provide compound of formula VIII;

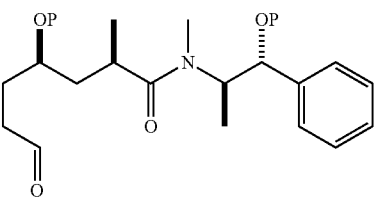

VIII wherein P is an alcohol protecting group;

(e) reacting compound of formula VIII with compound of formula IX to provide compound of formula X;

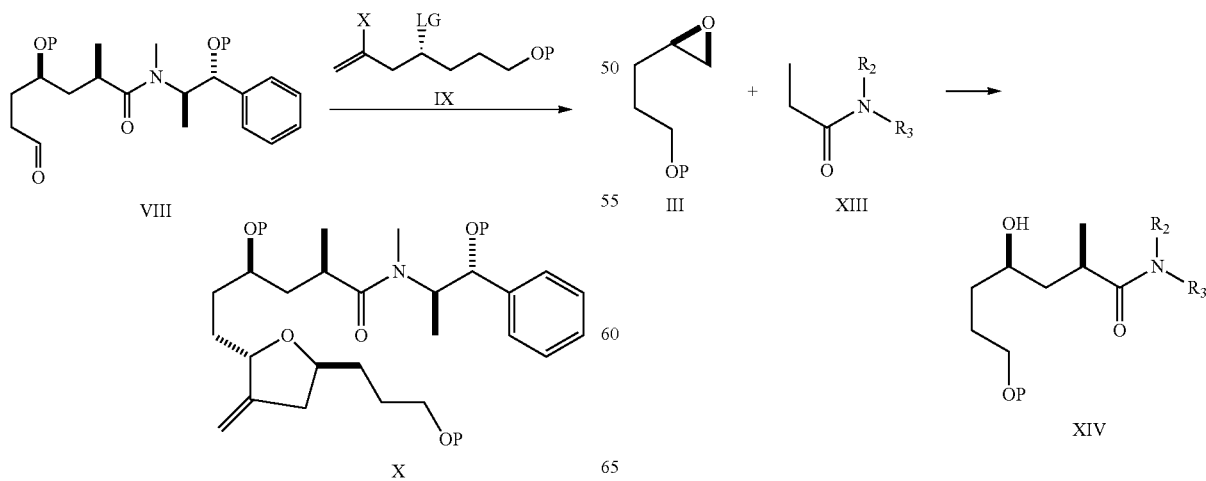

wherein P is an alcohol-protecting group; LG is —OSO$_2$(R$_1$); wherein R$_1$ is selected from straight or branched C$_1$-C$_{10}$ alkyl or optionally substituted C$_5$-C$_{12}$ aryl; X is halogen.

(f) converting compound of formula X to compound of formula XI; and

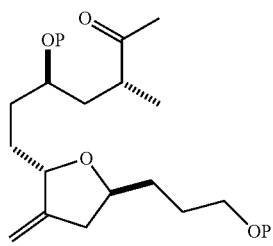

XI wherein P is an alcohol-protecting group;

(g) converting compound of formula XI to compound of formula II

In the second embodiment, the present application provides a process for preparation of 4-Methylene tetrahydrofuran compound of formula II,

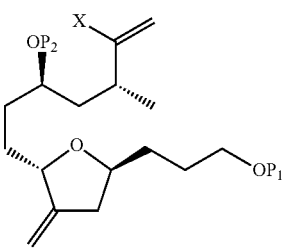

II wherein P$_1$ is H or an alcohol protecting group; P$_2$ is H or an alcohol protecting group or —SO$_2$(R$_1$); wherein R$_1$ is selected from straight or branched C$_1$-C$_{10}$ alkyl or optionally substituted C$_5$-C$_{12}$ aryl; X is halogen;

which includes one or more of the following steps:

(a) reacting compound of formula III with compound of formula XIII to provide compound of formula XIV;

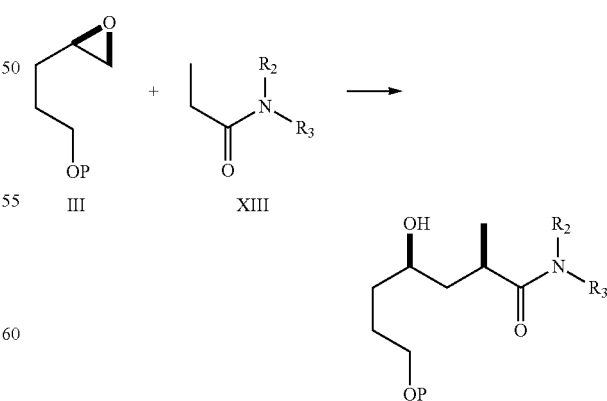

wherein P is an alcohol-protecting group; R$_2$, R$_3$ is same or different and are independently selected from hydrogen, alkyl, alkenyl, alkoxy, heteroalkyl, aryl, aralkyl, heteroaryl; all optionally substituted through available carbon atoms with 1, 2, 3, 4 or 5 groups selected from hydrogen, halo, alkyl, alkoxy, haloalkoxy, alkenyl, alkynyl, cycloalkyl, heteroalkyl, aryl, nitro, cyano, amino or substituted amino and the like or $R_2$ and $R_3$ together to form a 4-7 membered ring containing a 1-3 heteroatoms selected from N, O, S wherein one or more carbon or hetero atoms of the 4-7 membered ring optionally substituted with halo, alkyl, alkoxy, carbonyl, thiocarbonyl, haloalkoxy, alkenyl, alkynyl, cycloalkyl, heteroalkyl, aryl, nitro, cyano or amino; provided that when $R_2$ is methyl, then $R_3$ is not methoxy or when $R_3$ is methyl, then $R_2$ is not methoxy. For example, —$NR_2R_3$ include;

or stereoisomers thereof;

(b) protecting compound of formula XIV to provide compound of formula XV;

wherein P, $R_2$ and $R_3$ defined above;

(c) deprotecting compound of formula XV to provide compound of formula XVI;

wherein P, $R_2$ and $R_3$ defined above;

(d) converting compound of formula XVI to provide compound of formula XVII;

wherein P, $R_2$ and $R_3$ defined above;

(e) reacting compound of formula XVII with compound of formula IX to provide compound of formula XVIII;

wherein P is an alcohol-protecting group; LG is —$OSO_2$ ($R_1$); wherein $R_1$ is selected from straight or branched $C_1$-$C_{10}$ alkyl or optionally substituted $C_5$-$C_{12}$ aryl; X is halogen and $R_2$ and $R_3$ defined above;

(f) converting compound of formula XVIII to compound of formula XI; and

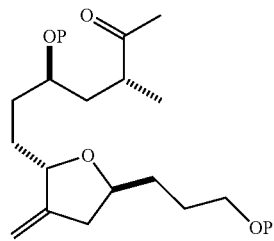

XI wherein P is an alcohol-protecting group;

(g) converting compound of formula XI to compound of formula II

In the third embodiment, the present application provides a compound of formula VI or a compound of formula VII or a compound of formula VIII or a compound of formula X or a compound of formula XI or a compound of formula XII or a compound of formula XIII or a compound of formula XIV or a compound of formula XV or a compound of formula XVI or a compound of formula XVII or a compound of formula XVIII or stereoisomers thereof.

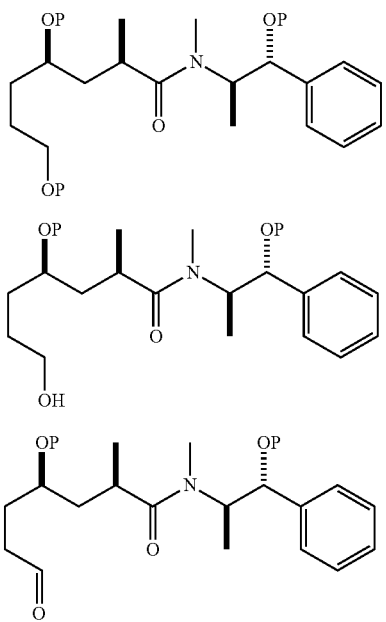

VI

VII

VIII

X

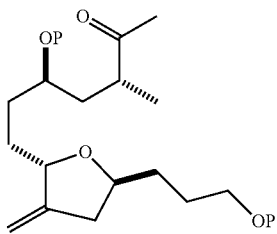

XI

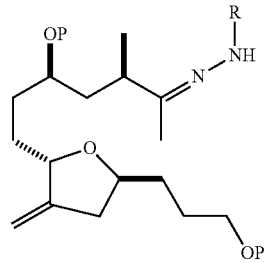

XII

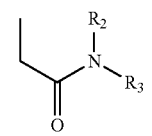

XIII

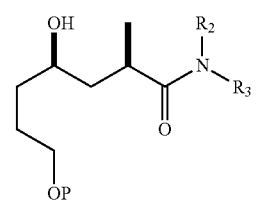

XIV

XV

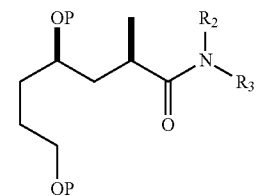

XVI

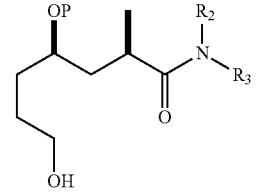

XVII

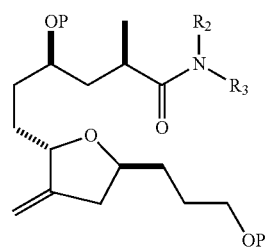

XVIII wherein P, R₁, R₂ and R₃ defined above; and R is H or —SO₂(R₁);

In the fourth embodiment, the present application provides a process for preparation of Eribulin or its pharmaceutically acceptable salts via a compound of formula VI or a compound of formula VII or a compound of formula VIII or a compound of formula X or a compound of formula XI or a compound of formula XII or a compound of formula XIII or a compound of formula XIV or a compound of formula XV or a compound of formula XVI or a compound of formula XVII or a compound of formula XVIII or a stereoisomers thereof.

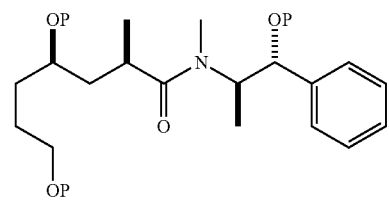

VI

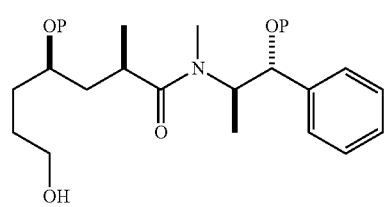

VII

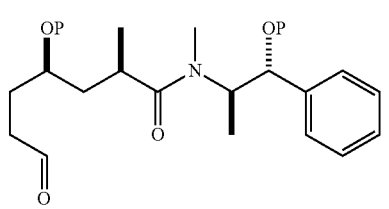

VIII

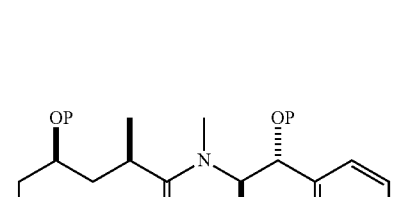

X

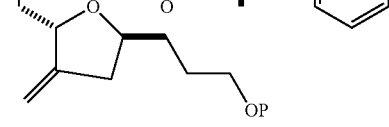

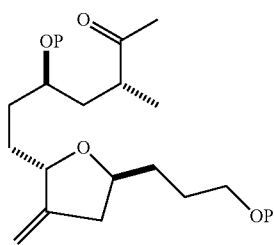

XI

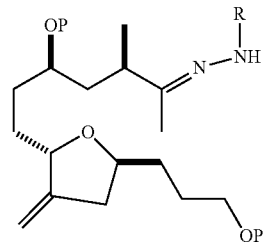

XII

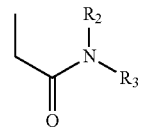

XIII

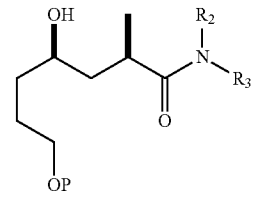

XIV

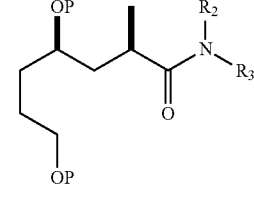

XV

XVI

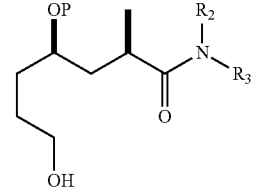

XVII

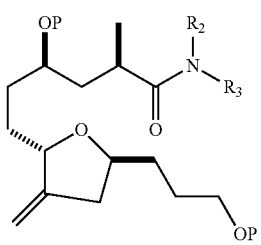

XVIII wherein P, R, $R_1$, $R_2$ and $R_3$ defined above;

In the fifth embodiment, the present application provides a purification process of compound of formula IIa, said process comprising;

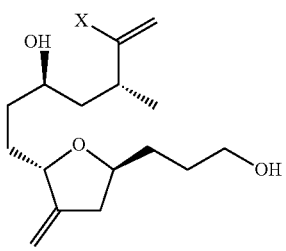

IIa (a) Reacting crude compound of formula IIa with a suitable derivatizing agent to give compound of formula IIb; and

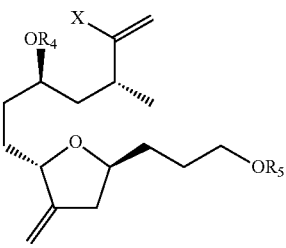

IIb wherein X is halogen, one of $R_4$ or $R_5$ is hydrogen, or $R_4$ and $R_5$ are independently selected from —C(O)—$R_6$ wherein $R_6$ is alkyl, heteroalkyl, aryl, aralkyl, heteroaryl; which are optionally substituted with groups selected from hydrogen, halo, alkyl, alkoxy, haloalkoxy, alkenyl, alkynyl, cycloalkyl, heteroalkyl, aryl, aralkyl, nitro, cyano, amino or substituted amino and the like, for example —C(O)—$R_6$ includes:

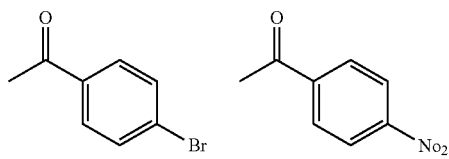

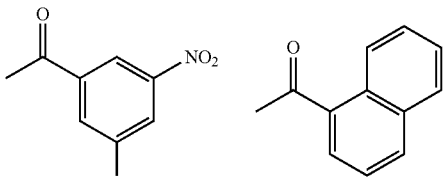

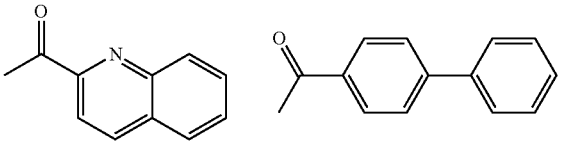

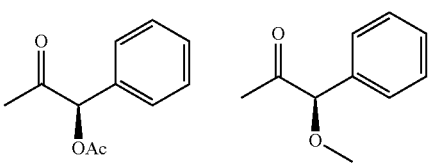

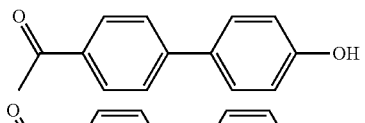

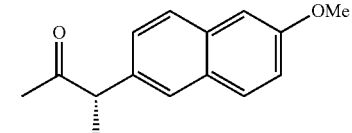

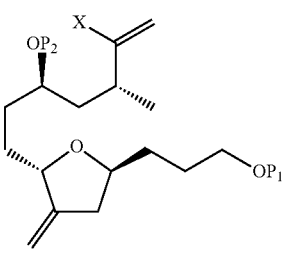

(b) optionally purifying compound of Formula IIb; and
(c) converting compound of formula IIb to compound of formula IIa.

DETAILED DESCRIPTION

In the first embodiment, the present application provides a process for preparation of 4-Methylene tetrahydrofuran compound of formula II,

II wherein $P_1$ is H or an alcohol protecting group; P2 is H or an alcohol protecting group or —$SO_2(R_1)$; wherein $R_1$ is selected from straight or branched $C_1$-$C_{10}$ alkyl or optionally substituted $C_5$-$C_{12}$ aryl; X is halogen;

which includes one or more of the following steps:
(a) reacting compound of formula III with compound of formula IV to provide compound of formula V;

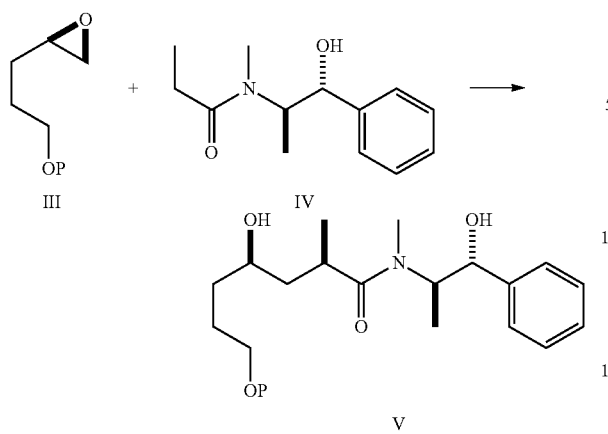

III + IV →

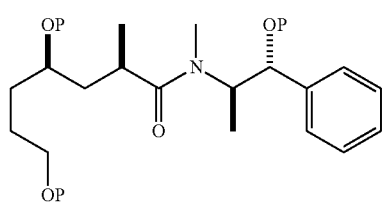

V wherein P is an alcohol-protecting group;

(b) protecting compound of formula V to provide compound of formula VI;

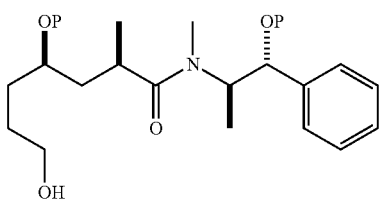

VI wherein P is an alcohol-protecting group;

(c) deprotecting compound of formula VI to provide compound of formula VII;

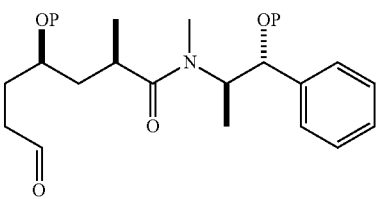

VII wherein P is an alcohol-protecting group;

(d) converting compound of formula VII to provide compound of formula VIII;

VIII wherein P is an alcohol protecting group;

(e) reacting compound of formula VIII with compound of formula IX to provide compound of formula X;

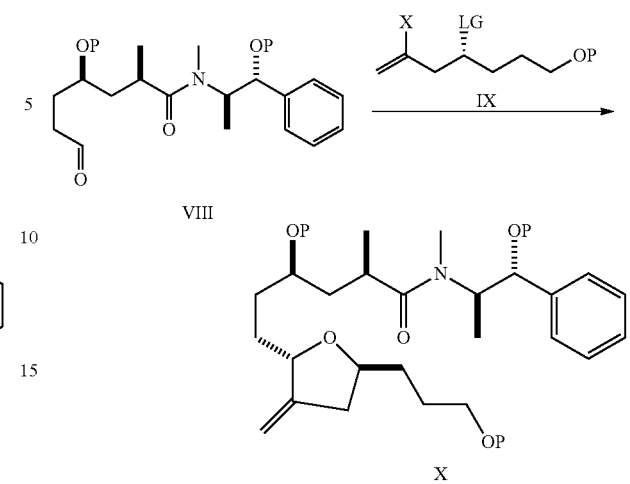

VIII + IX →

X wherein P is an alcohol-protecting group; LG is —OSO$_2$(R$_1$); wherein R$_1$ is selected from straight or branched C$_1$-C$_{10}$ alkyl or optionally substituted C$_5$-C$_{12}$ aryl; X is halogen.

(f) converting compound of formula X to compound of formula XI; and

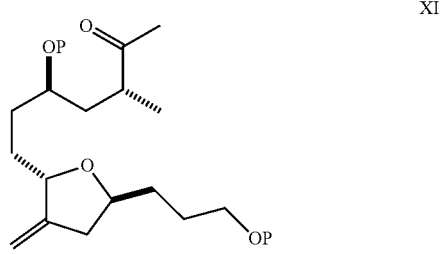

XI wherein P is an alcohol-protecting group;

(g) converting compound of formula XI to compound of formula II

Step (a) involves reacting compound of formula III with compound of formula IV to provide compound of formula V;

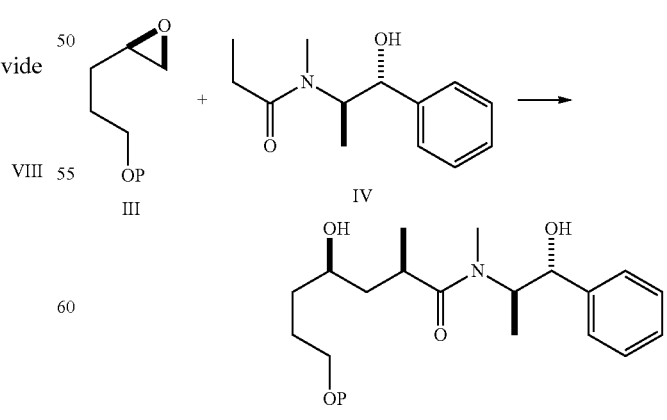

III + IV →

V wherein P is an alcohol-protecting group;

Suitable reagents that may be used in step (a) include n-Butyllithium, sec-Butyllithium, tert-Butyllithium, lithium bis(trimethylsilyl)amide, lithium diisopropylamide and the like or any other suitable reagents known in the art.

Suitable solvents that may be used in step (a) include ethers, aliphatic and alicyclic hydrocarbons, halogenated hydrocarbons, polar aprotic solvents or mixtures thereof.

The reaction mixture obtained from step (a) may be optionally processed to remove any insoluble solids, and particles may be removed by methods such as decantation, centrifugation, gravity filtration, suction filtration, or any other techniques for the removal of solids. The product of step (a) may be isolated directly from the reaction mixture itself after the reaction is complete in step (a), or after conventional work up with techniques such as filtration, quenching with a suitable reagent, extraction, or the like. Optionally, the resulting product may be directly used for step (b) with or without isolation or it may be further purified, if isolated, to improve the purity of the product.

Step (b) involves protecting compound of formula V to provide compound of formula VI;

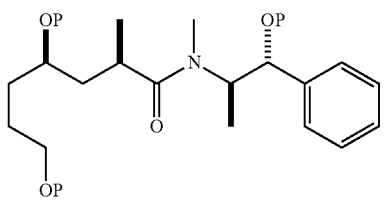

VI wherein P is an alcohol-protecting group;

Suitable base that may be used in step (c) include, alkali metal or alkaline earth metal hydroxides such as sodium hydroxide, potassium hydroxide, lithium hydroxide, calcium hydroxide; carbonates such as sodium carbonate, potassium carbonate, cesium carbonate, calcium carbonate, magnesium carbonate, sodium bicarbonate, potassium bicarbonate, alkoxides such as sodium methoxide, potassium methoxide; organic bases, such as for example, triethylamine, tributylamine, N-methylmorpholine, N,N-diisopropylethylamine, N-methylpyrrolidine, pyridine, collidine 4-(N,N-dimethylamino)pyridine, morpholine, imidazole, 2-methylimidazole, 4-methylimidazole and the like or any other suitable base known in the art.

Suitable solvents that may be used in step (b) include ketones, esters, ethers, aliphatic and alicyclic hydrocarbons, halogenated hydrocarbons, aromatic hydrocarbons, nitriles, polar aprotic solvents, nitromethane or mixtures thereof.

The reaction mixture obtained from step (b) may be optionally processed to remove any insoluble solids, and particles may be removed by methods such as decantation, centrifugation, gravity filtration, suction filtration, or any other techniques for the removal of solids. The product of step (b) may be isolated directly from the reaction mixture itself after the reaction is complete in step (b), or after conventional work up with techniques such as filtration, quenching with a suitable reagent, extraction, or the like. Optionally, the resulting product may be directly used for step (c) with or without isolation or it may be further purified, if isolated, to improve the purity of the product.

Step (c) involves deprotecting compound of formula VI to provide compound of formula VII;

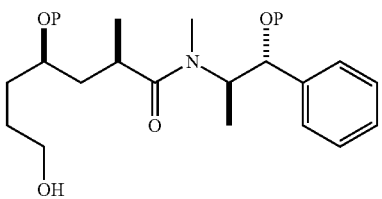

VII wherein P is an alcohol-protecting group;

Suitable reagents that may be used in step (c) include, hydrochloric acid, hydrobromic acid, hydroiodic acid, nitric acid, sulfuric acid, acetic acid, formic acid, phosphoric acid, methanesulfonic acid, p-toluenesulfonic acid, tetra-n-butylammonium fluoride (TBAF), pyridinium p-toluenesulfonate (PPTS), tris(dimethylamino)sulfonium difluorotrimethylsilicate, ammonia, sodium hydroxide, potassium hydroxide, sodium methoxide, potassium t-butoxide, sodium t-butoxide, sodium carbonate, potassium carbonate, sodium bicarbonate, potassium bicarbonate, and the like; ion exchange resins, such as: resins bound to metal ions, including lithium, sodium, potassium, and the like; and resins bound to acids, including phosphoric, sulfonic, methanesulfonic, p-toluenesulfonic, and the like or any other suitable reagents and mixtures thereof.

Suitable solvents that may be used in step (c) include water, alcohols, ketones, ethers, aliphatic and alicyclic hydrocarbons, halogenated hydrocarbons, aromatic hydrocarbons, nitriles, polar aprotic solvents, nitromethane or mixtures thereof.

Suitable temperature that may be used in step (c) may be less than about 120° C., less than about 90° C., less than about 70° C., less than about 40° C., less than about 30° C., less than about 10° C., less than about 0° C., less than about −10° C., less than about −20° C., or any other suitable temperature.

The reaction mixture obtained from step (c) may be optionally processed to remove any insoluble solids, and particles may be removed by methods such as decantation, centrifugation, gravity filtration, suction filtration, or any other techniques for the removal of solids. The product of step (c) may be isolated directly from the reaction mixture itself after the reaction is complete in step (c), or after conventional work up with techniques such as filtration, quenching with a suitable reagent, extraction, or the like. Optionally, the resulting product may be directly used for step (d) with or without isolation or it may be further purified, if isolated, to improve the purity of the product.

Step (d) involves converting compound of formula VII to provide compound of formula VIII;

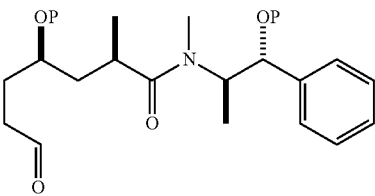

VIII wherein P is an alcohol protecting group;

Suitable reagents that may be used in step (d) include, (2,2,6,6-tetramethyl-piperidin-1-yl)oxyl (TEMPO), pyridinium chlorochromate (PCC), oxalyl chloride & dimethyl sulfoxide (DMSO), dicyclohexylcarbodiimide & DMSO, Dess-Martin periodinane, [Bis(acetoxy)iodo]-benzene (BAIB), manganese dioxide, (diacetoxyiodo)benzene, sulphurtrioxide-pyridine complex and the like or combination thereof or any other suitable oxidizing agent known in the art.

Suitable solvents that may be used in step (d) include, ethers, aliphatic and alicyclic hydrocarbons, aromatic hydrocarbons, halogenated hydrocarbons, polar aprotic solvents or mixtures thereof.

The reaction mixture obtained from step (d) may be optionally processed to remove any insoluble solids, and particles may be removed by methods such as decantation, centrifugation, gravity filtration, suction filtration, or any other techniques for the removal of solids. The product of step (d) may be isolated directly from the reaction mixture itself after the reaction is complete in step (d), or after conventional work up with techniques such as filtration, quenching with a suitable reagent, extraction, or the like. Optionally, the resulting product may be directly used for step (e) with or without isolation or it may be further purified, if isolated, to improve the purity of the product.

Step (e) involves reacting compound of formula VIII with compound of formula IX to provide compound of formula X;

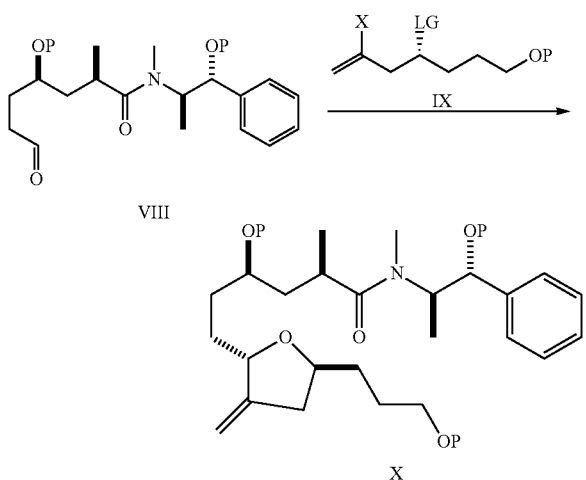

wherein P is an alcohol-protecting group; LG is —OSO$_2$(R); wherein R is selected from straight or branched C$_1$-C$_{10}$ alkyl or optionally substituted C$_5$-C$_{12}$ aryl; X is halogen.

Suitable reagents that may be used in step (e) include, chromium chloride and optionally a ligand such as '(R)—N-(2-(4-isopropyl-4,5-dihydrooxazol-2-yl)phenyl)methanesulfonamide and the like, nickel chloride and optionally a ligand such as 2,9-dimethyl-1,10-phenanthroline and the like or any other suitable catalyst or ligands known in the art used in Nozaki-Hiyama-Kishi (NHK) reaction.

Suitable bases that may be used in step (e) include, sodium hydride, potassium tert-butoxide, sodium methoxide, lithium hexamthyldisilazide, sodium amide, 1,8-bis(dimethylamino)naphthalene (Proton-sponge) and the like; other organic bases, such as for example, N-methylmorpholine, N-methylpyrrolidine, pyridine, 4-(N,N-dimethylamino)pyridine, morpholine, imidazole and the like or any other suitable base known in the art.

Suitable solvents that may be used in step (e) include, ethers, aliphatic and alicyclic hydrocarbons, aromatic hydrocarbons, nitriles, polar aprotic solvents or mixtures thereof.

The reaction mixture obtained from step (e) may be optionally processed to remove any insoluble solids, and particles may be removed by methods such as decantation, centrifugation, gravity filtration, suction filtration, or any other techniques for the removal of solids. The product of step (e) may be isolated directly from the reaction mixture itself after the reaction is complete in step (e), or after conventional work up with techniques such as filtration, quenching with a suitable reagent, extraction, or the like. Optionally, the resulting product may be directly used for step (f) with or without isolation or it may be further purified, if isolated, to improve the purity of the product.

Step (f) involves converting compound of formula X to compound of formula XI;

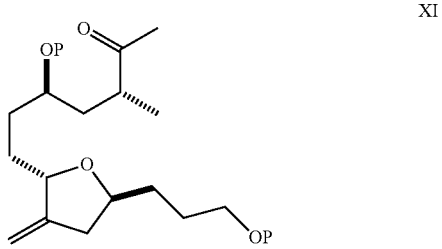

wherein P is an alcohol-protecting group;

Suitable solvents that may be used in step (f) include, esters, ethers, aliphatic and alicyclic hydrocarbons, aromatic hydrocarbons, nitriles, polar aprotic solvents or mixtures thereof.

The reaction mixture obtained from step (f) may be optionally processed to remove any insoluble solids, and particles may be removed by methods such as decantation, centrifugation, gravity filtration, suction filtration, or any other techniques for the removal of solids. The product of step (f) may be isolated directly from the reaction mixture itself after the reaction is complete in step (f), or after conventional work up with techniques such as filtration, quenching with a suitable reagent, extraction, or the like. Optionally, the resulting product may be directly used for step (g) with or without isolation or it may be further purified, if isolated, to improve the purity of the product.

Step (g) involves converting compound of formula XI to compound of formula II

Step (g) may be carried out in two steps. The first involves the conversion of methyl ketone compound of formula XI in to hydrazone compound of formula XII and the second step involves the conversion of compound of formula XII to vinyl halide compound of formula II.

Suitable reagents or catalysts that may be used in step (g) include the reagents or catalysts that are known in the art for Shapiro reaction or Barton iodination or any other suitable reagents or catalysts known in the art for the conversion of methyl ketone substrate to vinyl halide.

Suitable solvents that may be used in step (g) include, esters, ethers, aliphatic and alicyclic hydrocarbons, aromatic hydrocarbons, nitriles, polar aprotic solvents or mixtures thereof.

The reaction mixture obtained from step (g) may be optionally processed to remove any insoluble solids, and particles may be removed by methods such as decantation, centrifugation, gravity filtration, suction filtration, or any other techniques for the removal of solids. The product of step (g) may be isolated directly from the reaction mixture itself after the reaction is complete in step (g), or after conventional work up with techniques such as filtration, quenching with a suitable reagent, extraction, or the like. Optionally, the resulting product may be directly used for next step with or without isolation or it may be further purified, if isolated, to improve the purity of the product.

Optionally steps (a) to (g) or any two or more steps may be carried out as in-situ i.e. without isolating the intermediates in each stage.

In the second embodiment, the present application provides a process for preparation of 4-Methylene tetrahydrofuran compound of formula II,

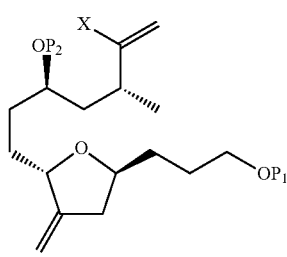

II wherein $P_1$ is H or an alcohol protecting group; $P_2$ is H or an alcohol protecting group or —$SO_2(R_1)$; wherein $R_1$ is selected from straight or branched $C_1$-$C_{10}$ alkyl or optionally substituted $C_5$-$C_{12}$ aryl; X is halogen;

which includes one or more of the following steps:
(a) reacting compound of formula III with compound of formula XIII to provide compound of formula XIV;

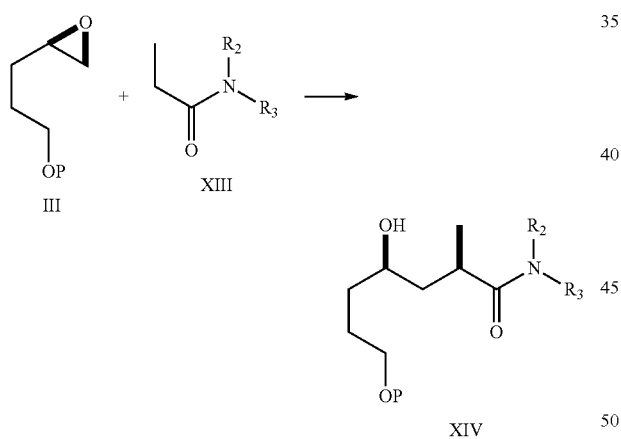

XIV wherein P is an alcohol-protecting group; $R_2$, $R_3$ is same or different and are independently selected from hydrogen, alkyl, alkenyl, alkoxy, heteroalkyl, aryl, aralkyl, heteroaryl; all optionally substituted through available carbon atoms with 1, 2, 3, 4 or 5 groups selected from hydrogen, halo, alkyl, alkoxy, haloalkoxy, alkenyl, alkynyl, cycloalkyl, heteroalkyl, aryl, nitro, cyano, amino or substituted amino and the like or $R_2$ and $R_3$ together to form a 4-7 membered ring containing a 1-3 heteroatoms selected from N, O, S wherein one or more carbon or hetero atoms of the 4-7 membered ring optionally substituted with halo, alkyl, alkoxy, carbonyl, thiocarbonyl, haloalkoxy, alkenyl, alkynyl, cycloalkyl, heteroalkyl, aryl, nitro, cyano or amino; provided that when $R_2$ is methyl, then $R_3$ is not methoxy or when $R_3$ is methyl, then $R_2$ is not methoxy. For example, —$NR_2R_3$ include

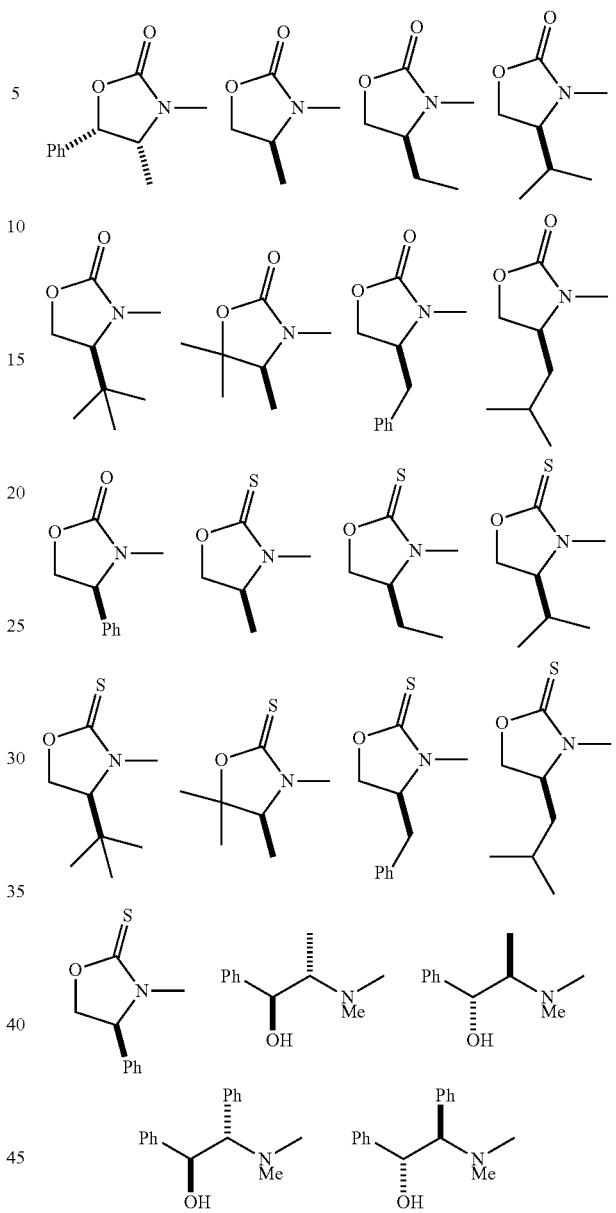

or stereoisomers thereof;
(b) protecting compound of formula XIV to provide compound of formula XV;

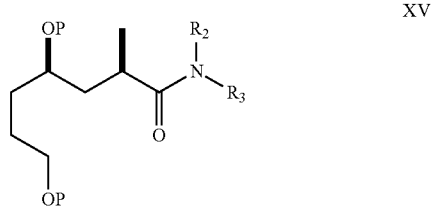

XV wherein P, $R_2$ and $R_3$ defined above;
(c) deprotecting compound of formula XV to provide compound of formula XVI;

XVI

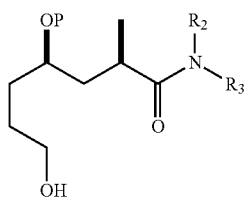

wherein P, R$_2$ and R$_3$ defined above;

(d) converting compound of formula XVI to provide compound of formula XVII;

XVII

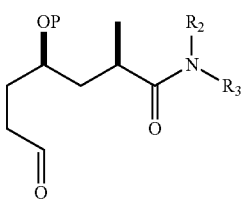

wherein P, R$_2$ and R$_3$ defined above;

(e) reacting compound of formula XVII with compound of formula IX to provide compound of formula XVIII;

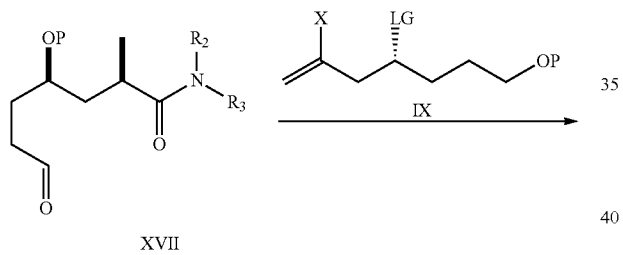

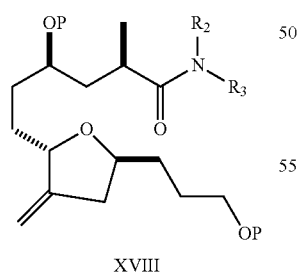

wherein P is an alcohol-protecting group; LG is —OSO$_2$ (R$_1$); wherein R$_1$ is selected from straight or branched C$_1$-C$_{10}$ alkyl or optionally substituted C$_5$-C$_{12}$ aryl; X is halogen and R$_2$ and R$_3$ defined above;

(f) converting compound of formula XVIII to compound of formula XI; and

XI

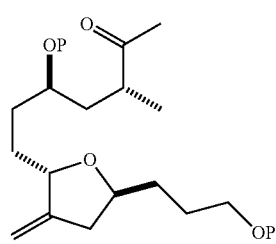

wherein P is an alcohol-protecting group;

(g) converting compound of formula XI to compound of formula II

In the third embodiment, the present application provides a compound of formula VI or a compound of formula VII or a compound of formula VIII or a compound of formula X or a compound of formula XI or a compound of formula XII or a compound of formula XIII or a compound of formula XIV or a compound of formula XV or a compound of formula XVI or a compound of formula XVII or a compound of formula XVIII or stereoisomers thereof.

VI

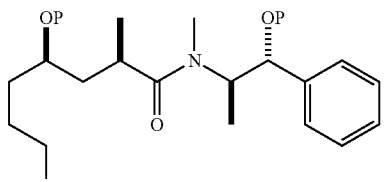

VII

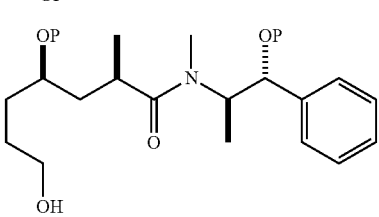

VIII

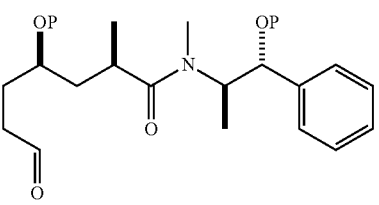

X

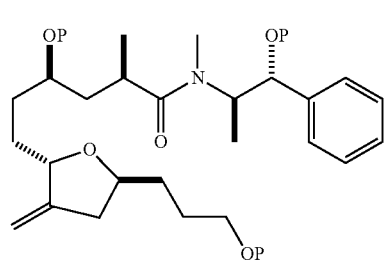

23
-continued

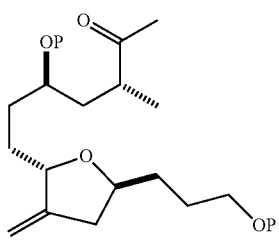

XI

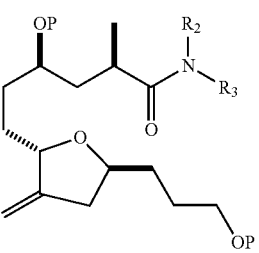

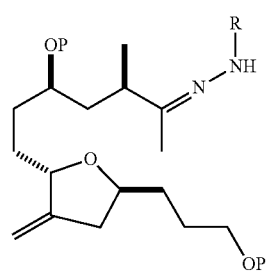

XII

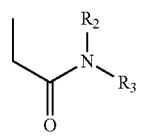

XIII wherein P, R, $R_1$, $R_2$ and $R_3$ defined above;

In the fourth embodiment, the present application provides a process for preparation of Eribulin or its pharmaceutically acceptable salts via a compound of formula VI or a compound of formula VII or a compound of formula VIII or a compound of formula X or a compound of formula XI or a compound of formula XII or a compound of formula XIII or a compound of formula XIV or a compound of formula XV or a compound of formula XVI or a compound of formula XVII or a compound of formula XVIII or stereoisomers thereof.

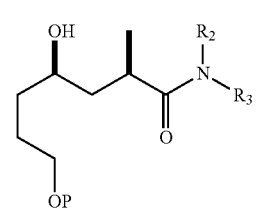

XIV

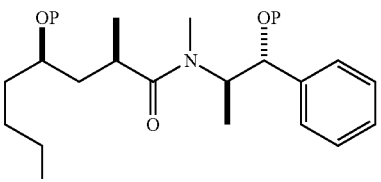

VI

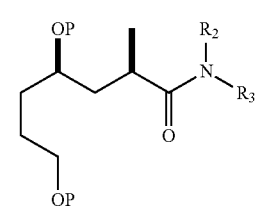

XV

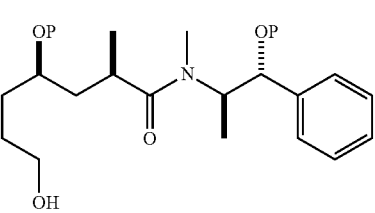

VII

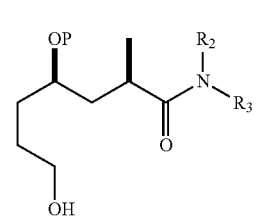

XVI

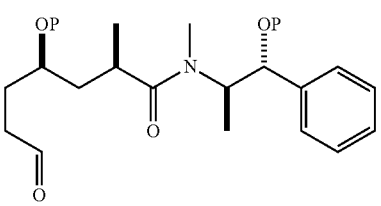

VIII

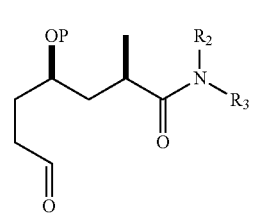

XVII

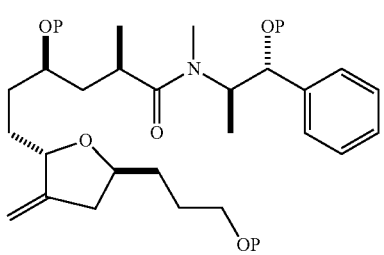

X

XI

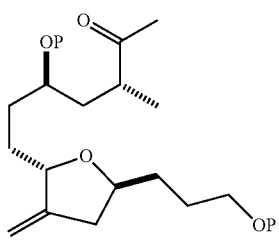

XII

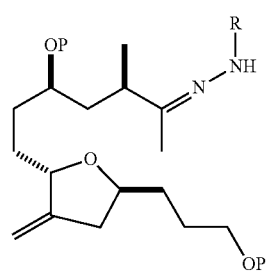

XIII

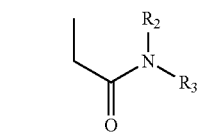

XIV

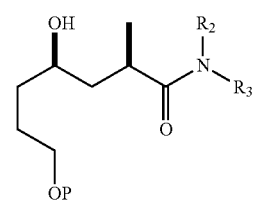

XV

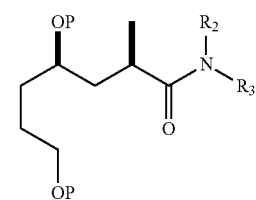

XVI

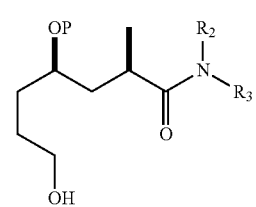

XVII

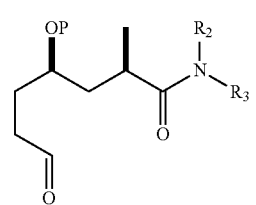

XVIII

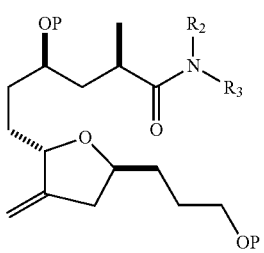

wherein P, R, $R_1$, $R_2$ and $R_3$ defined above;

In the fifth embodiment, the present application provides a purification process of compound of formula IIa, said process comprising:

IIa

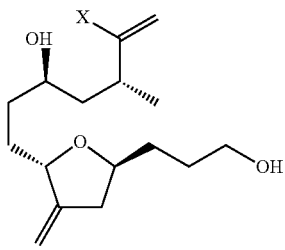

(a) Reacting crude compound of formula IIa with a suitable derivatizing agent to give compound of formula IIb; and IIb

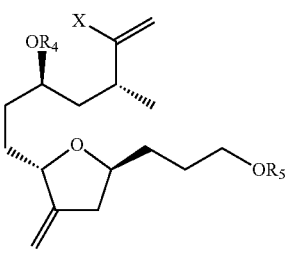

wherein X is halogen, one of $R_4$ or $R_5$ is hydrogen, or $R_4$ and $R_5$ are independently selected from —C(O)—$R_6$ wherein $R_6$ is alkyl, heteroalkyl, aryl, aralkyl, heteroaryl; which are optionally substituted with groups selected from hydrogen, halo, alkyl, alkoxy, haloalkoxy, alkenyl, alkynyl, cycloalkyl, heteroalkyl, aryl, aralkyl, nitro, cyano, amino or substituted amino and the like, for example —C(O)—$R_6$ includes:

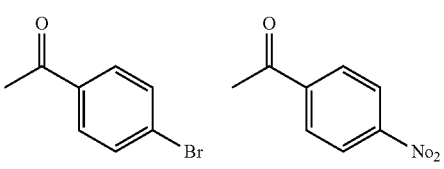

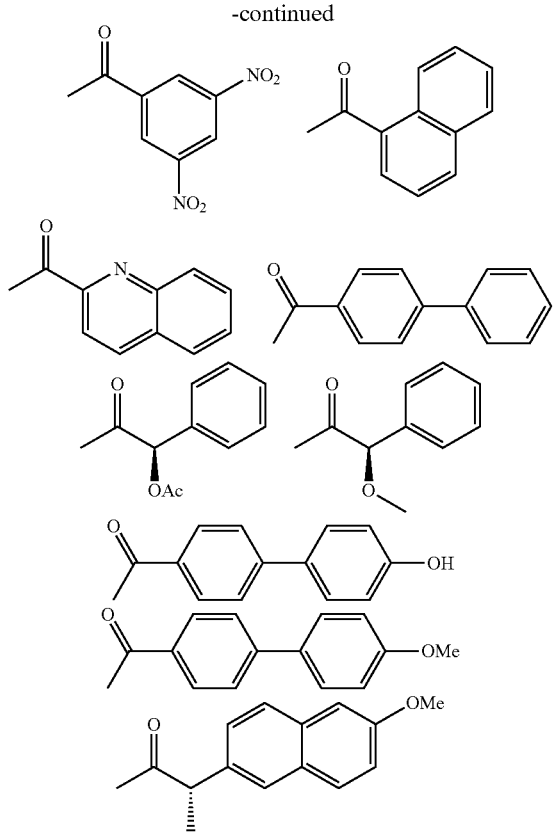

(b) optionally purifying compound of formula IIb; and
(c) converting compound of formula IIb to compound of formula IIa.

Step (a) involves reacting crude compound of formula IIa with a suitable derivatizing agent to give compound of formula IIb; and

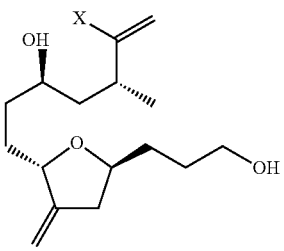

IIa

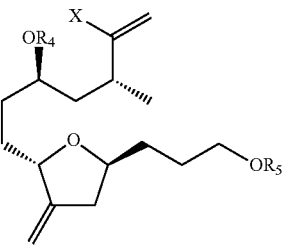

IIb

Suitable base that may be used in step (a) include, organic bases, such as for example, triethylamine, tributylamine, N-methylmorpholine, N,N-diisopropylethylamine, N-methylpyrrolidine, pyridine, collidine 4-(N,N-dimethylamino) pyridine, morpholine, imidazole, 2-methylimidazole, 4-methylimidazole and the like or any other suitable base known in the art.

Suitable solvents that may be used in step (a) include ketones, esters, ethers, aliphatic and alicyclic hydrocarbons, halogenated hydrocarbons, aromatic hydrocarbons, nitriles, polar aprotic solvents, nitromethane or mixtures thereof.

The reaction mixture obtained from step (a) may be optionally processed to remove any insoluble solids, and particles may be removed by methods such as decantation, centrifugation, gravity filtration, suction filtration, or any other techniques for the removal of solids. The product of step (a) may be isolated directly from the reaction mixture itself after the reaction is complete in step (a), or after conventional work up with techniques such as filtration, quenching with a suitable reagent, extraction, or the like. Optionally, the resulting product may be directly used for step (b) with or without isolation or it may be further purified.

Step (b) involves optionally purifying compound of formula IIb.

Purification may be carried out by recrystallization, slurrying in a suitable solvent, acid-base treatment, column chromatography, treating with adsorbent materials such as, but not limited to, silica gel, aluminium oxide, synthetic resin, and the like; or any other suitable techniques known in the art.

Step (c) involves converting compound of formula IIb to compound of formula IIa.

Suitable reagents that may be used in step (c) include, hydrochloric acid, hydrobromic acid, hydroiodic acid, nitric acid, sulfuric acid, acetic acid, formic acid, phosphoric acid, methanesulfonic acid, p-toluenesulfonic acid, tetra-n-butylammonium fluoride (TBAF), pyridinium p-toluenesulfonate (PPTS), tris(dimethylamino)sulfonium difluorotrimethylsilicate, ammonia, sodium hydroxide, potassium hydroxide, sodium methoxide, potassium t-butoxide, sodium t-butoxide, sodium carbonate, potassium carbonate, sodium bicarbonate, potassium bicarbonate, and the like; metals such as magnesium and the like, ion exchange resins, such as: resins bound to metal ions, including lithium, sodium, potassium, and the like; and resins bound to acids, including phosphoric, sulfonic, methanesulfonic, p-toluenesulfonic, and the like or any other suitable reagents and mixtures thereof.

Suitable solvents that may be used in step (c) include water, alcohols, ketones, ethers, aliphatic and alicyclic hydrocarbons, halogenated hydrocarbons, aromatic hydrocarbons, nitriles, polar aprotic solvents, nitromethane or mixtures thereof.

Suitable temperature that may be used in step (c) may be less than about 120° C., less than about 90° C., less than about 70° C., less than about 40° C., less than about 30° C., less than about 10° C., less than about 0° C., less than about −10° C., less than about −20° C., or any other suitable temperature.

The reaction mixture obtained from step (c) may be optionally processed to remove any insoluble solids, and particles may be removed by methods such as decantation, centrifugation, gravity filtration, suction filtration, or any other techniques for the removal of solids. The product of step (c) may be isolated directly from the reaction mixture itself after the reaction is complete in step (c), or after conventional work up with techniques such as filtration, quenching with a suitable reagent, extraction, or the like.

Definitions

The following definitions are used in connection with the present application unless the context indicates otherwise. In general, the number of carbon atoms present in a given group or compound is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions or the like.

As used herein, "an alcohol protecting group" is a functional group that protects the alcohol group from participating in reactions that are occurring in other parts of the molecule. Suitable alcohol protecting groups that are used in step (a) include, acetyl, benzoyl, benzyl, β-methoxyethoxymethyl ether, methoxymethyl ether, dimethoxytrityl, p-methoxybenzyl ether, methylthiomethyl ether, allyl ether, t-butyl ether, pivaloyl, trityl, silyl ether (e.g., trimethylsilyl (TMS), t-butyldimethylsilyl (TBMDS), t-butyldiphenylsilyl (TBDPS), t-butyldimethylsilyloxymethyl (TOM) or triisopropylsilyl (TIPS) ether), tetrahydropyranyl (THP), methyl ether and ethoxyethyl ether (EE) or any suitable alcohol protecting group known in the art. Alcohol protecting groups used for protecting As used herein, the term "lower alkyl", "alkyl" or "alk" includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof.

As used herein, the term "lower alkenyl" or "alkenyl" as used by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

As used herein, the term "halogen" or "halo" as used herein alone or as part of another group refers to chlorine, bromine, fluorine, and iodine.

As used herein, the term "aryl" as alone or as part of another group refers to monocyclic and bicyclic aromatic groups containing 6 to 10 carbons in the ring portion such as phenyl or naphthyl including 1-naphthyl and 2-naphthyl and the like.

As used herein, the term "lower alkoxy", "alkoxy", "aryloxy" or "aralkoxy" as alone or as part of another group includes any of the above alkyl, aralkyl or aryl groups linked to an oxygen atom.

As used herein, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides.

An "alcohol" is an organic compound containing a carbon bound to a hydroxyl group. "$C_1$-$C_6$ alcohols" include methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, phenol, glycerol and the like.

An "aliphatic hydrocarbon" is a liquid hydrocarbon compound, which may be linear, branched, or cyclic and may be saturated or have as many as two double bonds. A liquid hydrocarbon compound that contains a six-carbon group having three double bonds in a ring is called "aromatic." Examples of "$C_5$-$C_8$ aliphatic or aromatic hydrocarbons" include n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, petroleum ethers, benzene toluene, ethylbenzene, m-xylene, o-xylene, p-xylene, trimethylbenzene, chlorobenzene, fluorobenzene, trifluorotoluene, anisole, and the like.

An "aromatic hydrocarbon solvent" refers to a liquid, unsaturated, cyclic, hydrocarbon containing one or more rings which has delocalized conjugated π system. Examples of an aromatic hydrocarbon solvent include benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{12}$ aromatic hydrocarbons and the like.

An "ester" is an organic compound containing a carboxyl group —(C=O)—O-bonded to two other carbon atoms. "$C_3$-$C_6$ esters" include ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate and the like.

An "ether" is an organic compound containing an oxygen atom —O— bonded to two other carbon atoms. "$C_2$-$C_6$ ethers" include diethyl ether, diisopropyl ether, methyl t-butyl ether, glyme, diglyme, tetrahydrofuran, 2-methyltetrahydrofuran, 1, 4-dioxane, dibutyl ether, dimethylfuran, 2-methoxyethanol, 2-ethoxyethanol, anisole and the like.

A "halogenated hydrocarbon" is an organic compound containing a carbon bound to a halogen. Halogenated hydrocarbons include dichloromethane, 1,2-dichloroethane, trichloroethylene, perchloroethylene, 1,1,1-trichloroethane, 1,1,2-trichloroethane, chloroform, carbon tetrachloride and the like.

A "ketone" is an organic compound containing a carbonyl group —(C=O)— bonded to two other carbon atoms. "$C_3$-$C_6$ ketones" include acetone, ethyl methyl ketone, diethyl ketone, methyl isobutyl ketone, ketones and the like.

A "nitrile" is an organic compound containing a cyano —(C≡N) bonded to another carbon atom. "$C_2$-$C_6$ Nitriles" include acetonitrile, propionitrile, butanenitrile and the like.

A "polar aprotic solvents" include N, N-dimethylformamide, N, N-dimethylacetamide, dimethylsulfoxide, sulfolane, N-methylpyrrolidone and the like;

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present application. While particular aspects of the present application have been illustrated and described, it would be obvious to those skilled in the art that various other changes and modifications can be made without departing from the spirit and scope of the invention. It is therefore intended to cover in the appended claims all such changes and modifications that are within the scope of this application.

EXAMPLES

Example-1: Preparation of (2R,4R)-7-((tert-butyldimethylsilyl)oxy)-4-hydroxy-N-((1R,2R)-1-hydroxy-1-phenylpropan-2-yl)-N,2-dimethylheptanamide Lithium chloride (47 g) charged in to a round bottom flask, heated to 135° C. under reduced pressure (4 Torr) and stirred at 135° C. for 2 hours 15 minutes. Tetrahydrofuran (600 mL) was added to the lithium chloride at 25° C. under argon atmosphere and cooled to −78° C. Diisopropylamine (54.4 mL), n-Butyllithium (2.5M in Hexane; 155.3 mL) was added at −78° C. and the resultant reaction mixture was stirred at −78° C. for 15 minutes and at 0° C. for 35 minutes. N-((1R,2R)-1-hydroxy-1-phenylpropan-2-yl)-Nmethylpropionamide (40.9 g) was added at −78° C. and stirred at −78° C. for 1 hour 20 minutes. Reaction mass temperature slowly increased to 25° C. and cooled back to 0° C. (R)-tert-butyldimethyl(3-(oxiran-2-yl)propoxy)silane(40 g) slowly added to the reaction mass at 0° C. and stirred at 25° C. for 10 hours. Aqueous ammonium chloride solution (400 mL) was slowly added to the reaction mass at 0° C. Ethyl acetate (200 mL) was added to the reaction mass at 25° C. and stirred for 15 minutes. Layers were separated, aqueous layer was extracted with ethyl acetate (2×100 mL), the combined organic layer was washed with water (200 mL) and concentrated in vacuo. The obtained compound was purified by column chromatography using EtOAc/hexane to afford titled compound (70.8 g).

Example-2: Preparation of (2R,4R)-4,7-bis((tert-butyldimethylsilyl)oxy)-N-((1R,2R)-1-((tertbutyldimethylsilyl)oxy)-1-phenylpropan-2-yl)-N,2-dimethylheptan amide Imidazole (27.5 g) was added to the reaction mass containing (2R,4R)-7-((tert-butyldimethylsilyl)oxy)-4-hydroxy-N-((1R,2R)-1-hydroxy-1-phenylpropan-2-yl)-N,2-dimethylheptanamide (70.8 g) dimethylformamide (560 mL) at 0° C. under argon atmosphere. Tert-butylchlorodimethylsilane (52.4 g) was added to the reaction mass at 0° C. and the resultant reaction mass was stirred at 25° C. for 15 hours 30 minutes. Anhydrous methanol (50 mL) was added to the reaction mass at 25° C. and cooled to 4° C. Aqueous ammonium chloride solution (600 mL) was added to the reaction mass at 4° C. and stirred for 10 minutes. Layers were separated and aqueous layer was extracted with ethyl acetate (100 mL). The combined organic layer was washed with water (2×100 mL), dried over NaSO₄ and concentrated in vacuo to afford titled compound (107 g).

Example-3: Preparation of (2R,4R)-4-((tert-butyldimethylsilyl)oxy)-N-((1R,2R)-1-((tertbutyldimethylsilyl)oxy)-1-phenylpropan-2-yl)-7-hydroxy-N,2-Dimethylheptan amide Pyridinium-p-Toluene sulphonate (0.47 g) was added to the reaction mass containing 2R,4R)-4,7-bis((tert-butyldimethylsilyl)oxy)-N-((1R,2R)-1-((tert-butyldimethyl silyl) oxy)-1-phenylpropan-2-yl)-N,2-dimethylheptanamide (50 g), isopropyl alcohol (480 mL) and water (16 mL) at 25° C. and the resultant reaction mass was stirred at 25° C. for 8 hours 30 minutes. Sodium bicarbonate solution (60 mL) was added to the reaction mass at 25° C. and concentrated in vacuo at below 42° C. Ethyl acetate (200 mL) and water (50 mL) was added to the reaction mass and stirred for 10 minutes. Layers were separated and aqueous layer was extracted with ethyl acetate (50 mL). The combined organic layer was washed with brine solution (30 mL), dried over NaSO₄ and concentrated in vacuo. The obtained compound was purified by column chromatography using EtOAc/hexane to afford titled compound (18.5 g).

Example-4: Preparation of (2R,4R)-4-((tert-butyldimethylsilyl)oxy)-N-((1R,2R)-1-((tertbutyldimethylsilyl)oxy)-1-phenylpropan-2-yl)-N,2-dimethyl-7-oxoheptanamide Dess-Martin Periodinane (29.2 g) was added to the reaction mass containing (2R,4R)-4-((tert-butyldimethylsilyl)oxy)-N-((1R,2R)-1-((tert-butyldimethylsilyl)oxy)-1-phenylpropan-2-yl)-7-hydroxy-N,2-Dimethylheptan amide (19 g) and dichloromethane (380 mL) at 25° C. and the resultant reaction mass was stirred at 25° C. for 1 hour. Aqueous sodium carbonate solution (400 mL) and sodium sulfite solution (400 mL) was added to the reaction mass at 27° C. Reaction mass extracted with dichloromethane (2×100 mL), combined organic layer dried over NaSO₄ and concentrated in vacuo. The obtained compound was purified by column chromatography using EtOAc/hexane to afford titled compound (15.8 g).

Example-5: Preparation of (2R,4R)-4-((tert-butyldimethylsilyl)oxy)-N-((1R,2R)-1-((tertbutyldimethylsilyl)oxy)-1-phenylpropan-2-yl)-6-((2S,5S)-5-(3-((tert-butyl dimethylsilyl)oxy)propyl)-3-methylenetetrahydrofuran-2-yl)-N,2-dimethylhexan amide Triethylamine (8.59 g) was slowly added to the reaction mass containing (R)—N-(2-(4-isopropyl-4,5-dihydrooxazol-2-yl)-6-methylphenyl)methanesulfonamide (25.1 g), tetrahydrofuran (220 mL) and chromium chloride (10.35 g). Nickel chloride (0.278 g) was added portion wise at 25° C. A solution of (2R,4R)-4-((tert-butyldimethylsilyl)oxy)-N-((1R,2R)-1-((tertbutyldimethylsilyl)oxy)-1-phenylpropan-2-yl)-N,2-dimethyl-7-oxo heptanamide (10 g) and (R)-2-bromo-7-((tert-butyldimethylsilyl)oxy)hept-1-en-4-yl-2,4,6-triisopropylbenzenesulfonate (13.94 g) in tetrahydrofuran (60 mL) was added slowly to the reaction mass at 25° C. and the resultant reaction mass stirred at 25° C. for 7 hours 30 minutes. Ethylenediamine (14.57 g) was added drop wise to the reaction mass at 0° C. and stirred at 0° C. for 1 hour. Water (120 mL) was added drop wise to the reaction mass at 25° C. and stirred for 30 minutes. Heptane (200 mL) was added to the reaction mass at 25° C. and stirred for 10 minutes. Layers were separated, aqueous layer extracted with heptane (2×100 mL), methyl tert-butyl ether (2×100 mL). The combined organic layers washed with sodium bicarbonate (2×250 mL) solution, sodium chloride solution (2×250 mL) and concentrated in vacuo. Isopropyl alcohol (330 mL) and silica gel (33 g) was added to the crude compound and stirred at 25° C. for 16 hours. Reaction mass was filtered, silica was washed with isopropyl alcohol and the obtained filtrate concentrated in vacuo. Acetonitrile (150 mL) was added to the compound and the resultant acetonitrile layer was extracted with heptane (5×100 mL). Evaporated all the heptane layer and the obtained crude material was purified using column chromatography to afford title compound (8.2 g).

Example-6: Preparation of (3R,5R)-5-((tert-butyldimethylsilyl)oxy)-7-((2S,5S)-5-(3-((tertbutyldimethylsilyl)oxy)propyl)-3-methylenetetrahydrofuran-2-yl)-3-methyl heptan-2-one Methyl lithium (3.1 M in Diethoxymethane; 10.83 mL) was added to the reaction mass containing (2R,4R)-4-((tert-butyldimethylsilyl)oxy)-N-((1R,2R)-1-((tertbutyl dimethylsilyl)oxy)-1-phenylpropan-2-yl)-6-((2S,5S)-5-(3-((tert-butyldimethylsilyl)oxy) propyl)-3-methylene tetrahydrofuran-2-yl)-N,2-dimethylhexan amide (8 g) and tetrahydrofuran (80 mL) at −78° C. The resultant reaction mass temperature slowly increased to 0° C. and stirred at 0° C. for 30 minutes. Saturated ammonium chloride solution (80 mL) was added to the reaction mass at 0° C. and stirred for 10 minutes. Reaction mass was extracted with ethyl acetate (2×80 mL) and concentrated in vacuo. The obtained compound was purified by column chromatography using EtOAc/hexane to afford titled compound (4.4 g).

Example-7: Preparation of (E)-N'-((3R,5R)-5-((tert-butyldimethylsilyl)oxy)-7-((2S,5S)-5-(3-((tert-butyldimethylsilyl)oxy)propyl)-3-methylenetetrahydrofuran-2-yl)-3-methylheptan-2-ylidene)-2,4,6-triisopropylbenzenesulfonohydrazide 2,4,6-triisopropylbenzenesulfonohydrazide (3.13 g) was added to the reaction mass containing (3R,5R)-5-((tert-butyldimethylsilyl)oxy)-7-((2S,5S)-5-(3-((tertbutyldimethylsilyl)oxy)propyl)-3-methylenetetrahydrofuran-2-yl)-3-methyl heptan-2-one (3.26 g) and tetrahydrofuran (30 mL) at 0° C. and the resultant reaction mass was stirred at 27° C. for 20 hours. Sodium sulphate (5 g) was added to the reaction mass at 27° C., the reaction mass was filtered and washed with hexane (50 mL). Filtrate concentrated in vacuo and the obtained compound was purified by column chromatography using EtOAc/hexane to afford titled compound (4.86 g).

Example-8: Preparation of tert-butyl(3-((2S,5S)-5-((3R,5R)-3-((tert-butyldimethyl silyl)oxy)-6-iodo-5-methylhept-6-en-1-yl)-4-methylenetetrahydrofuran-2-yl) propoxy) dimethylsilane n-Butyllithium (2.5 M in hexane; 109 g) was added drop wise to the reaction mass containing (E)-N'-((3R,5R)-5-((tert-butyldimethylsilyl)oxy)-7-((2S,5S)-5-(3-((tert-butyl dimethylsilyl)oxy)propyl)-3-methylenetetrahydrofuran-2-yl)-3-methylheptan-2-ylidene)-2,4,6-triisopropylbenzenesulfonohydrazide (350 mg) and tetrahydrofuran (8 mL) at −78° C. under argon atmosphere and the resultant reaction mass was stirred at 0° C. for 15 minutes. Iodine (336 mg dissolved in 3.5 mL of tetrahydrofuran) was added slowly to the reaction mass at −78° C. and stirred at 0° C. for 30 minutes. Saturated sodium sulfite solution (5 mL) was added to the reaction mass at 0° C. Ethyl acetate (25 mL) was added to the reaction mass at 25° C. and stirred for 10 minutes. Layers separated, aqueous layer extracted with ethyl acetate (20 mL). The combined organic layer washed with aqueous sodium sulfite solution (10 mL) and concentrated in vacuo to afford titled compound.

Example-9: Preparation of ((3R,5R)-5-((tert-butyldimethylsilyl)oxy)-7-((2S,5S)-5-(3-((tert-butyldimethylsilyl)oxy)propyl)-3-methylenetetrahydrofuran-2-yl)-3-methyl heptan-2-ylidene)hydrazine Hydrazine hydrate (4.29 g), ethanol (45 mL) and (3R,5R)-5-((tert-butyldimethylsilyl)oxy)-7-((2S,5S)-5-(3-((tert-butyldimethylsilyl)oxy)propyl)-3-methylene tetrahydrofuran-2-yl)-3-methylheptan-2-one (4.4 g) charged in to a round bottom flask and stirred at 80° C. for 1 hour. Methanol (40 mL) was added to the reaction mass at 31° C. and concentrated in vacuo. The obtained compound was diluted with water (50 mL) and extracted with ethyl acetate (2×100 mL). The combined organic layer was washed with brine (1×20 mL) and dried over NaSO$_4$. The resultant organic layer passed through a small plug of silica gel, washed with ethyl acetate (5×30 mL) and the combined organic layer concentrated in vacuo to afford titled compound.

Example-10: Preparation of tert-butyl(3-((2S,5S)-5-((3R,5R)-3-((tert-butyldimethylsilyl)oxy)-6-iodo-5-methylhept-6-en-1-yl)-4-methylenetetrahydrofuran-2-yl) propoxy) dimethylsilane Triethylamine (43.4 g) was added to the reaction mass containing ((3R,5R)-5-((tert-butyldimethylsilyl)oxy)-7-((2S,5S)-5-(3-((tertbutyldimethylsilyl)oxy)propyl)-3-methylene tetrahydrofuran-2-yl)-3-methyl heptan-2-ylidene)hydrazine (4.52 g) and tetrahydrofuran (60 mL) at 5° C. under argon atmosphere. Solution of iodine (5.44 g in 10 mL of anhydrous tetrahydrofuran) was slowly added to the reaction mass at 5° C. and the resultant reaction mass was stirred at 24° C. for 1 hour. Saturated aqueous sodium sulfite solution (20 mL) was added to the reaction mass at 31° C. Reaction mass was diluted with water (100 mL) and extracted with ethyl acetate (3×100 mL). The combined organic layer was washed with water (1×100 mL), brine solution (1×50 mL) and dried over anhydrous sodium sulfate. The resultant organic layer passed through a small plug of silica gel, washed with ethyl acetate (5×30 mL) and the combined organic layer concentrated in vacuo. The obtained compound was purified by column chromatography using EtOAc/hexane to afford titled compound (3.37 g).

Example-11: Preparation of (3R,5R)-6-iodo-5-methyl-1-((2S,5S)-3-methylene-5-(3-((4-nitrobenzoyl)oxy)propyl)tetrahydrofuran-2-yl)hept-6-en-3-yl 4-nitrobenzoate Triethylamine (1.4 mL) was added to the reaction mass containing (3R,5R)-1-((2S,5S)-5-(3-hydroxypropyl)-3-methylenetetrahydrofuran-2-yl)-6-iodo-5-methylhept-6-en-3-ol (1 g; Purity By HPLC: 79.6%) and dichloromethane (20 mL) at 1° C. N,N-dimethylpyridin-4-amine (0.12 g) and 4-nitrobenzoyl chloride (1.412 g) was added to the reaction mass at 1° C. and the resultant reaction mass was stirred at 27° C. for 21 hours. Reaction mass was quenched with water and extracted with dichloromethane (2×20 mL). Organic layer was washed with 1N HCl solution, saturated sodium bicarbonate solution and dried over NaSO$_4$. The resultant organic layer concentrated in vacuo and the obtained compound was purified by column chromatography using EtOAc/hexane (yield: 1.82 g).

The resultant crude compound (710 mg) was suspended in heptane (11.5 mL) at 30° C. and stirred at 30° C. for 10 minutes. Methyl tert-butyl ether (6 mL) was added and stirred at 30° C. for 20 minutes. Seed (10 mg) was added to the reaction mass and stirred at 30° C. for 3 hours. Separated solid was filtered and washed with heptane (2×2 mL) and dried. (Purity by HPLC: 92.4%).

The resultant compound (200 mg; Purity by HPLC: 92.4%) was dissolved in methyl tert-butyl ether (0.9 mL) at 31° C. and stirred for 10 minutes. Heptane (1 mL) was added at 31° C. and stirred at 31° C. for 5 minutes. Seed was added to the reaction mass and stirred at 31° C. for 2 hours. Separated solid was filtered and washed with heptane (2×2 mL) and dried to afford title compound. (Purity by HPLC: 93.2%).

Example-12: Preparation of (3S,5R)-1-((2S,5S)-5-(3-hydroxypropyl)-3-methylenetetrahydrofuran-2-yl)-6-iodo-5-methyl hept-6-en-3-ol (3R,5R)-6-iodo-5-methyl-1-((2S,5S)-3-methylene-5-(3-((4-nitrobenzoyl)oxy) propyl) tetrahydrofuran-2-yl)hept-6-en-3-yl 4-nitrobenzoate (200 mg; Purity by HPLC: 90.5%), methanol (20 mL) and Potassium carbonate (0.032 g) charged into round bottom flask at 27° C. and the resultant reaction mass was stirred at 27° C. for 6 hours. Acetic acid was added to the reaction mass concentrated in vacuo. The obtained compound was purified by column chromatography using EtOAc/hexane to afford titled compound (Purity by HPLC: 89.37%).

Example-13: Preparation of 3-((2S,5S)-5-((3R,5R)-3-(((1,1-biphenyl]-4-carbonyl) oxy)-6-iodo-5-methylhept-6-en-1-yl)-4-methylenetetrahydrofuran-2-yl) propyl [1,1'-biphenyl]-4-carboxylate N,N-dimethylpyridin-4-amine (0.774 g) was added to the reaction mass containing (3R,5R)-1-((2S,5S)-5-(3-hydroxypropyl)-3-methylenetetrahydrofuran-2-yl)-6-iodo-5-methylhept-6-en-3-ol (5 g; Purity by HPLC: 79.6%) and dichloromethane (75 mL) under an argon atmosphere at 4° C. Triethylamine (7.7 g) was added to the reaction mass at 2° C. [1,1'-biphenyl]-4-carbonyl chloride (10.98 g) was added to the reaction mass at 0° C. and the resultant reaction mass was stirred at 28° C. for 18 hours. N,N-dimethylpyridin-4-amine (0.619 g) was added to the reaction mass at 27° C. for 3 hours. 1M aqueous hydrochloride solution (40 mL) was slowly added to the reaction mass at 4° C. and stirred for 10 minutes. Organic layer separated and washed with water (20 mL). Aqueous NaHCO$_3$ solution (40 mL) was added to the organic layer at 27° C. and stirred for 15 minutes. Organic layer was separated, washed with brine solution (20 mL), dried over anhydrous sodium sulfate and concentrated in vacuo. The resultant crude compound was purified by column chromatography two times using EtOAc/hexane.

The obtained compound (8.28 g; Purity by HPLC: 82.33%) was dissolved in 10% EtOAc/Hexane (166 mL) at 58° C. and allowed to cool to 28° C. Seed compound (5 mg) was added at 27° C. and stirred at 22° C. for 1 hour 30 minutes. Separated solid was filtered and dried (Purity by HPLC: 90.49%). The obtained compound (5.44 g; purity by HPLC: 90.49%) and ethyl acetate (10.88 mL) was added at 28° C. and stirred at 28° C. for 1 hour. n-Hexane (97.9 mL) was added to the reaction mass at 28° C. and the resultant reaction mass was heated to 58° C. Reaction mass was cooled to 8° C. and stirred for 1 hour 30 minutes. Separated solid was filtered, washed with mixture of ethyl acetate (0.5 mL) and n-hexane (10.3 mL) and dried to afford title compound. (Purity by HPLC: 92.84%).

Example-14: Preparation of (3R,5R)-1-((2S,5S)-5-(3-hydroxypropyl)-3-methylenetetrahydrofuran-2-yl)-6-iodo-5-methyl hept-6-en-3-ol Lithium hydroxide monohydrate solution (0.067 g of lithium hydroxide dissolved in 0.6 mL water) was added to the reaction mass containing 3-((2S,5S)-5-((3R,5R)-3-(((1,1'-biphenyl]-4-carbonyl)oxy)-6-iodo-5-methylhept-6-en-1-yl)-4-methylenetetrahydrofuran-2-yl)propyl [1,1'-biphenyl]-4-carboxylate (300 mg; Purity by HPLC: 89.05%), tetrahydrofuran (1.8 mL) & methanol (0.6 mL) at 28° C. and stirred at 28° C. for 24 hours. The resultant reaction mass was concentrated in vacuo, dichloromethane (20 mL) was added to the crude compound and aqueous ammonium chloride solution (5 mL). Organic layer was separated, washed with 1M sodium hydroxide solution (2×10 mL), brine solution (10 mL) and dried over anhydrous sodium sulfate. Organic layer concentrated in vacuo and the resultant compound was purified by column chromatography using EtOAc/hexane to afford title compound (Purity by HPLC: 91.43%)

The invention claimed is:

1. A process for preparation of 4-Methylene tetrahydrofuran compound of formula II an intermediate in the synthesis of eribulin, said process comprising:

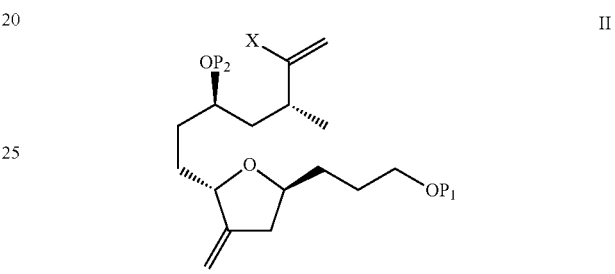

wherein $P_1$ is H or an alcohol protecting group; $P_2$ is H or an alcohol protecting group or —$SO_2(R_1)$; wherein $R_1$ is selected from straight or branched $C_1$-$C_{10}$ alkyl or optionally substituted $C_5$-$C_{12}$ aryl; X is halogen;

(a) reacting compound of formula III with compound of formula XIII to provide compound of formula XIV;

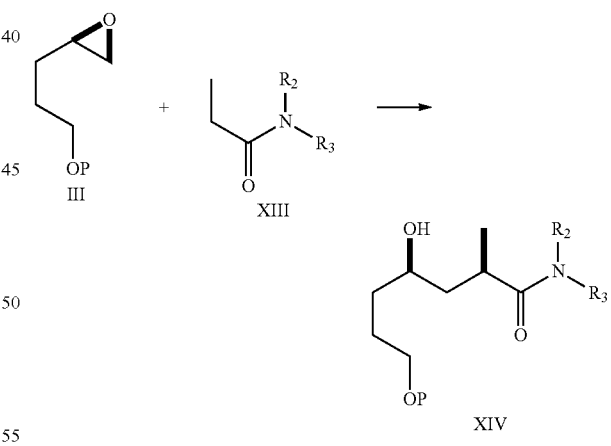

wherein P is an alcohol-protecting group; $R_2$, $R_3$ is same or different and are independently selected from hydrogen, alkyl, alkenyl, alkoxy, heteroalkyl, aryl, aralkyl, heteroaryl; all optionally substituted through available carbon atoms with 1, 2, 3, 4 or 5 groups selected from hydrogen, halo, alkyl, alkoxy, haloalkoxy, alkenyl, alkynyl, cycloalkyl, heteroalkyl, aryl, nitro, cyano, amino or substituted amino or $R_2$ and $R_3$ together to form a 4-7 membered ring containing a 1-3 heteroatoms selected from N, O, S wherein one or more carbon or hetero atoms of the 4-7 membered ring optionally substituted with halo, alkyl, alkoxy, carbonyl, thiocarbonyl, haloalkoxy, alkenyl, alkynyl, cycloalkyl, heteroalkyl, aryl, nitro, cyano or amino; provided that when $R_2$ is methyl, then $R_3$ is not methoxy or when $R_3$ is methyl, then $R_2$ is not methoxy;

(b) protecting compound of formula XIV to provide compound of formula XV;

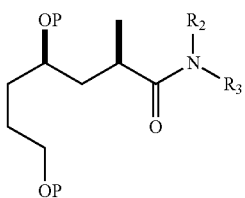

XV wherein P, $R_2$ and $R_3$ are as defined above;

(c) deprotecting compound of formula XV to provide compound of formula XVI;

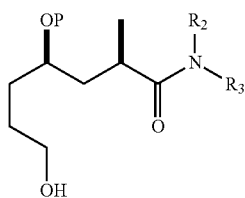

XVI wherein P, $R_2$ and $R_3$ are as defined above;

(d) converting compound of formula XVI to provide compound of formula XVII;

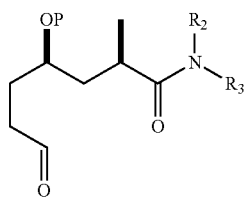

XVII wherein P, $R_2$ and $R_3$ are as defined above;

(e) reacting compound of formula XVII with compound of formula IX to provide compound of formula XVIII;

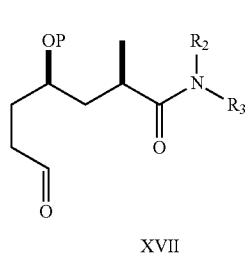 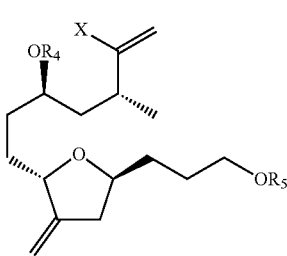

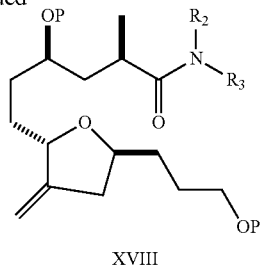

XVIII wherein P is an alcohol-protecting group; LG is —OSO$_2$(R$_1$); wherein R$_1$ is selected from straight or branched C$_1$-C$_{10}$ alkyl or optionally substituted C$_5$-C$_{12}$ aryl; X is halogen and R$_2$ and R$_3$ as defined above;

(f) converting compound of formula XVIII to compound of formula XI;

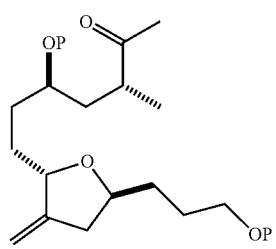

XI wherein P is an alcohol-protecting group; and (g) converting compound of formula XI to compound of formula II.

2. A purification process of compound of formula IIa, said process comprising;

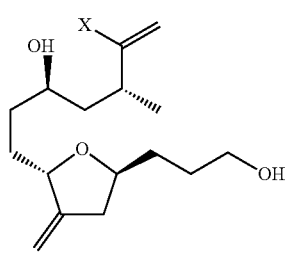

IIa (a) reacting crude compound of formula IIa with a suitable derivatizing agent to give compound of formula IIb;

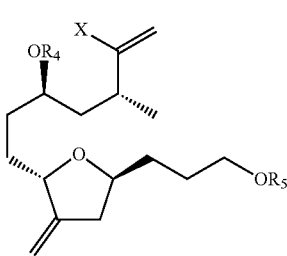

IIb wherein X is halogen, one of $R_4$ or $R_5$ is hydrogen, or $R_4$ and $R_5$ are independently selected from —C(O)—$R_6$ wherein $R_6$ is alkyl, heteroalkyl, aryl, aralkyl, heteroaryl; which are optionally substituted with groups selected from hydrogen, halo, alkyl, alkoxy, haloalkoxy, alkenyl, alkynyl, cycloalkyl, heteroalkyl, aryl, aralkyl, nitro, cyano, amino or substituted amino (b) optionally purifying compound of formula IIb; and
(c) converting compound of formula IIb to compound of formula IIa.

3. A compound having the following formula

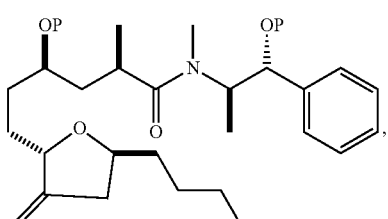

X

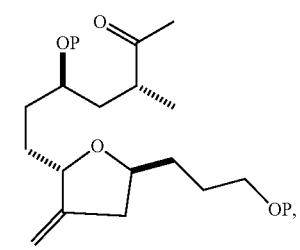

XI

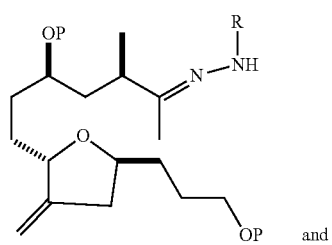

XII

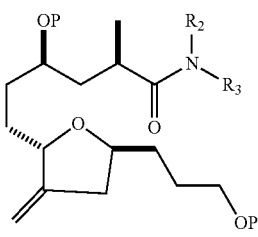 and

XVIII or isomers thereof, wherein P is an alcohol-protecting group, with the proviso that P in compound of formula XI is not a trityl (Tr) or tert-Butyldiphenylsilyl (TBDPS); R is H or —$SO_2(R_1)$; wherein $R_1$ is selected from straight or branched $C_1$-$C_{10}$ alkyl or optionally substituted $C_5$-$C_{12}$ aryl; $R_2$, $R_3$ is same or different and are independently selected from hydrogen, alkyl, alkenyl, alkoxy, heteroalkyl, aryl, aralkyl, heteroaryl; all optionally substituted through available carbon atoms with 1, 2, 3, 4 or 5 groups selected from hydrogen, halo, alkyl, alkoxy, haloalkoxy, alkenyl, alkynyl, cycloalkyl, heteroalkyl, aryl, nitro, cyano, amino or substituted amino or $R_2$ and $R_3$ together to form a 4-7 membered ring containing a 1-3 heteroatoms selected from N, O, S wherein one or more carbon or hetero atoms of the 4-7 membered ring optionally substituted with halo, alkyl, alkoxy, carbonyl, thiocarbonyl, haloalkoxy, alkenyl, alkynyl, cycloalkyl, heteroalkyl, aryl, nitro, cyano or amino; provided that when $R_2$ is methyl, then $R_3$ is not methoxy or when $R_3$ is methyl, then $R_2$ is not methoxy.

4. The process according to claim 1, further comprising converting the compound of formula II to eribulin of formula I or a pharmaceutically acceptable salt thereof,

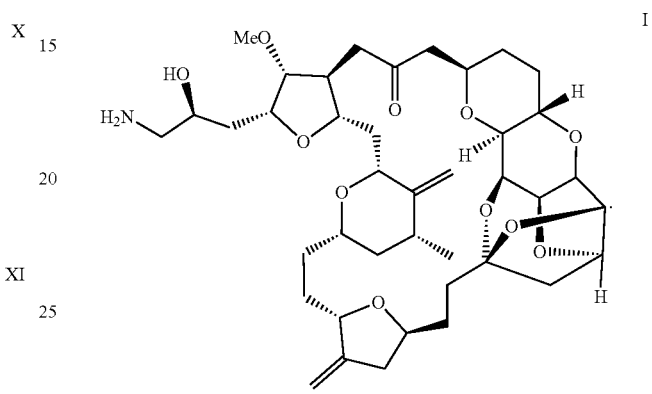

I

5. The process according to claim 1, wherein —$NR_2R_3$ is selected from:

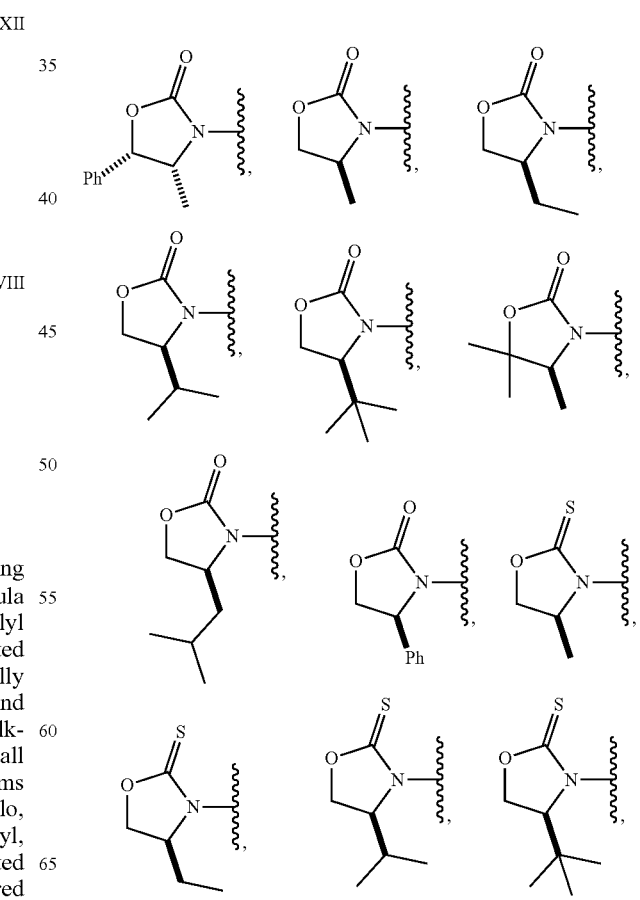

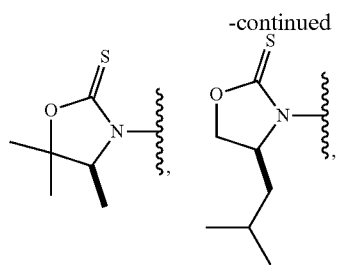

or stereoisomers thereof.

6. A process for preparation of 4-Methylene tetrahydrofuran compound of formula II comprising:

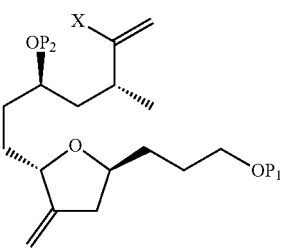

wherein $P_1$ is H or an alcohol protecting group; $P_2$ is H or an alcohol protecting group or —SO$_2$(R$_1$); wherein R$_1$ is selected from straight or branched C$_1$-C$_{10}$ alkyl or optionally substituted C$_5$-C$_{12}$ aryl; X is halogen;

(a) reacting compound of formula III with compound of formula IV to provide compound of formula V;

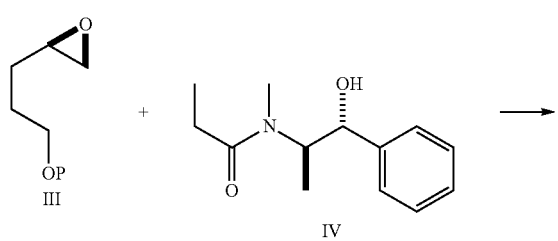

wherein P is an alcohol-protecting group;

(b) protecting compound of formula V to provide compound of formula VI;

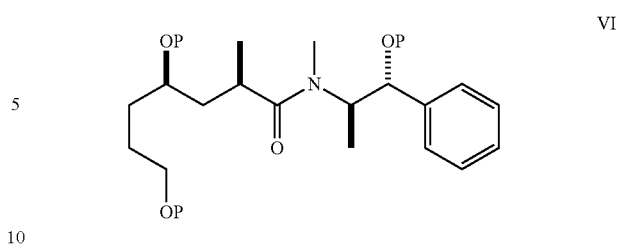

wherein P is an alcohol-protecting group;

(c) deprotecting compound of formula VI to provide compound of formula VII;

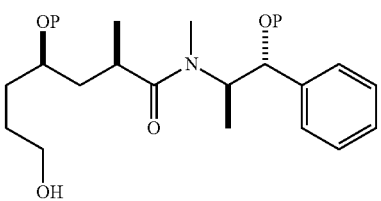

wherein P is an alcohol-protecting group;

(d) converting compound of formula VII to provide compound of formula VIII;

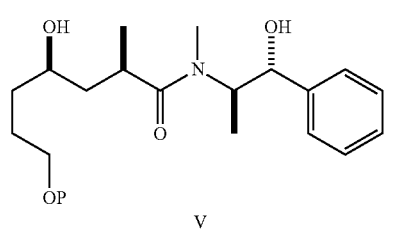

wherein P is an alcohol protecting group;

(e) reacting compound of formula VIII with compound of formula IX to provide compound of formula X;

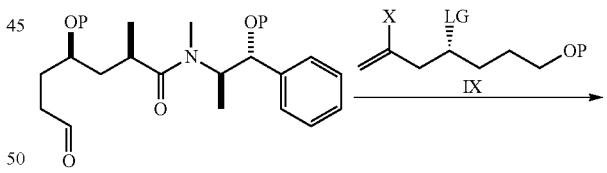

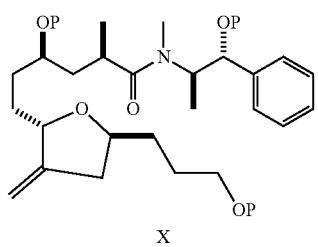

wherein P is an alcohol-protecting group; LG is —OSO$_2$(R$_1$); wherein R$_1$ is selected from straight or branched C$_1$-C$_{10}$ alkyl or optionally substituted C$_5$-C$_{12}$ aryl; X is halogen;

(f) converting compound of formula X to compound of formula XI;

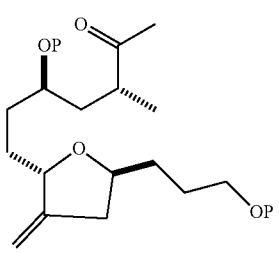
XI
wherein P is an alcohol-protecting group; and
(g) converting compound of formula XI to compound of formula II.
7. The process according to claim 2, wherein —C(O)—R$_6$ selected from:
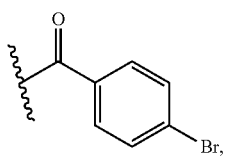 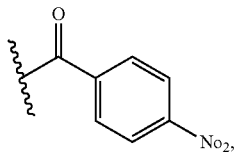
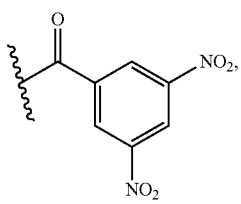 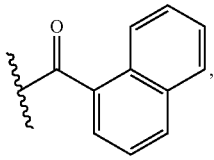
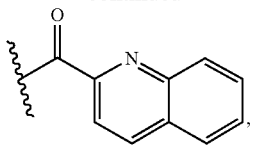
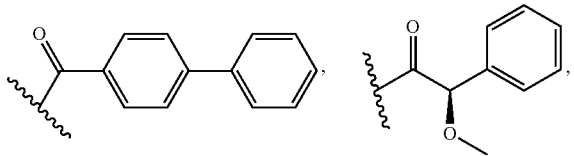
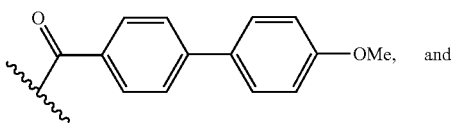
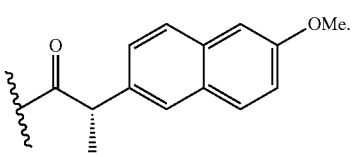
* * * * *